United States Patent
Gill et al.

(10) Patent No.: US 9,364,426 B2
(45) Date of Patent: Jun. 14, 2016

(54) METHOD OF MAKING COATED MICROSTRUCTURES

(71) Applicant: Georgia Tech Research Corporation, Atlanta, GA (US)

(72) Inventors: Harvinder Singh Gill, Lubbock, TX (US); Mark R. Prausnitz, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 103 days.

(21) Appl. No.: 14/185,725

(22) Filed: Feb. 20, 2014

(65) Prior Publication Data

US 2014/0170299 A1 Jun. 19, 2014

Related U.S. Application Data

(62) Division of application No. 11/917,705, filed as application No. PCT/US2006/023814 on Jun. 19, 2006, now abandoned.

(60) Provisional application No. 60/691,857, filed on Jun. 17, 2005, provisional application No. 60/732,267, filed on Nov. 1, 2005.

(51) Int. Cl.
*B05D 1/32* (2006.01)
*A61K 9/00* (2006.01)
(Continued)

(52) U.S. Cl.
CPC .......... *A61K 9/0021* (2013.01); *A61M 37/0015* (2013.01); *B05D 5/00* (2013.01); *A61K 9/0097* (2013.01); *A61M 2037/0046* (2013.01); *A61M 2037/0053* (2013.01); *B05D 1/32* (2013.01)

(58) Field of Classification Search
CPC .............. A61N 1/30; B05D 5/00; B05D 1/32; A61F 2/00; B44D 1/52; A61K 9/70; A61K 9/0097
USPC ............. 604/21, 173; 427/2.3, 2.14; 424/426, 424/449; 117/6
See application file for complete search history.

(56) References Cited

U.S. PATENT DOCUMENTS

| | | | |
|---|---|---|---|
| 3,964,482 | A | 6/1976 | Gerstel et al. |
| 4,832,797 | A | 5/1989 | Vadgama et al. |

(Continued)

FOREIGN PATENT DOCUMENTS

| | | |
|---|---|---|
| JP | 2005021678 | 1/2005 |
| WO | 0207813 A1 | 1/2002 |

(Continued)

OTHER PUBLICATIONS

Widera, Georg et al, Effect of delivery parameters on immunization to ovalbumin following intracutaneous administration by a coated microneedle array patch system, Elsevier, Vaccine 24 (2006) 1653-1664.

(Continued)

*Primary Examiner* — Andrew Bowman
(74) *Attorney, Agent, or Firm* — Sutherland Asbill & Brennan LLP

(57) ABSTRACT

Coated microneedle devices and methods of making such devices are provided. In one aspect, a method for coating includes providing a microstructure having at least one surface in need of coating; and applying a coating liquid, which includes at least one drug, to the at least one surface of the microstructure, wherein the surface energy of the coating liquid is less than the surface energy of the surface of the microstructure. The coating liquid may include a viscosity enhancer and surfactant. Microneedles having heterogeneous coatings, pockets, or both are also provided.

24 Claims, 9 Drawing Sheets

(51) Int. Cl.
B05D 5/00 (2006.01)
A61M 37/00 (2006.01)

(56) References Cited

U.S. PATENT DOCUMENTS

| | | | |
|---|---|---|---|
| 5,547,467 | A | 8/1996 | Pliquett et al. |
| 5,667,491 | A | 9/1997 | Pliquett et al. |
| 5,911,223 | A | 6/1999 | Weaver et al. |
| 6,107,004 | A | 8/2000 | Donadio, III |
| 6,334,856 | B1 | 1/2002 | Allen et al. |
| 6,451,240 | B1 | 9/2002 | Sherman et al. |
| 6,503,231 | B1 | 1/2003 | Prausnitz et al. |
| 6,611,707 | B1 | 8/2003 | Prausnitz et al. |
| 6,627,246 | B2 | 9/2003 | Mehta et al. |
| 6,641,831 | B1 | 11/2003 | Schierholz |
| 6,652,581 | B1 | 11/2003 | Ding |
| 6,743,211 | B1 | 6/2004 | Prausnitz et al. |
| 6,770,480 | B1 | 8/2004 | Canham |
| 6,855,372 | B2 * | 2/2005 | Trautman ............ A61B 17/205 427/2.31 |
| 7,226,439 | B2 | 6/2007 | Prausnitz et al. |
| 7,247,312 | B1 | 7/2007 | Sano et al. |
| 7,273,458 | B2 | 9/2007 | Prausnitz et al. |
| 7,344,499 | B1 | 3/2008 | Prausnitz et al. |
| 7,846,488 | B2 | 12/2010 | Johnson et al. |
| 2002/0009485 | A1 | 1/2002 | Di Cosmo et al. |
| 2002/0082543 | A1 * | 6/2002 | Park et al. .................. 604/21 |
| 2002/0169411 | A1 | 11/2002 | Sherman et al. |
| 2002/0177839 | A1 | 11/2002 | Cormier et al. |
| 2003/0109647 | A1 | 6/2003 | Lang et al. |
| 2004/0049150 | A1 | 3/2004 | Dalton et al. |
| 2004/0062813 | A1 | 4/2004 | Cormier et al. |
| 2004/0178388 | A1 | 9/2004 | Mumper et al. |
| 2004/0265365 | A1 | 12/2004 | Daddona et al. |
| 2005/0042240 | A1 | 2/2005 | Utterberg et al. |
| 2005/0137525 | A1 | 6/2005 | Wang et al. |
| 2005/0158382 | A1 | 7/2005 | Cruz et al. |
| 2005/0197308 | A1 | 9/2005 | Dalton et al. |
| 2005/0209565 | A1 | 9/2005 | Yuzhakov et al. |
| 2005/0261632 | A1 | 11/2005 | Xu |
| 2006/0084942 | A1 | 4/2006 | Kim et al. |
| 2006/0086689 | A1 | 4/2006 | Raju |
| 2006/0177494 | A1 | 8/2006 | Cormier et al. |
| 2007/0073197 | A1 | 3/2007 | Prausnitz et al. |
| 2007/0224252 | A1 | 9/2007 | Trautman et al. |
| 2007/0225676 | A1 | 9/2007 | Prausnitz et al. |
| 2008/0009825 | A1 | 1/2008 | Ringsred et al. |
| 2008/0027384 | A1 | 1/2008 | Wang et al. |
| 2008/0045879 | A1 | 2/2008 | Prausnitz et al. |
| 2008/0063866 | A1 | 3/2008 | Allen et al. |
| 2010/0280457 | A1 | 11/2010 | Tokumoto et al. |

FOREIGN PATENT DOCUMENTS

| | | |
|---|---|---|
| WO | 2004033021 A1 | 4/2004 |
| WO | 2005000382 | 1/2005 |
| WO | 2006004595 | 1/2006 |
| WO | 2006022933 A2 | 3/2006 |
| WO | 2006055799 A1 | 5/2006 |
| WO | 2006055844 A2 | 5/2006 |
| WO | 2006138719 | 12/2006 |
| WO | 2008011625 | 1/2008 |
| WO | 2010042996 | 4/2010 |

OTHER PUBLICATIONS

Chen, Xianfeng et al, Dry-coated microprojection array patches for targeted delivery of immunotherapeutics ot the skin, Nanomedicine, Journal of Controlled Release 139 (2009) 212-220.
PCT/US2006/023814, International Search Report and Written Opinion (2007).
PCT/US2006/023814, International Preliminary Report on Patentability (2007).
Gill & Prausnitz, Coated microneedles for transdermal delivery, J Controlled Release 117(2): 227-37 (2007).
Gill & Prausnitz, Coating Formulations for Microneedles, Pharm Res 24(7):1369-80 (2007).
Henry et al., Microfabricated microneedles: a novel method to increase transdermal drug delivery,J Pharm Sci 87: 922-25 (1998).
Kaushik et al., Lack of Pain Associated with Microfabricated Microneedles, Anesth Analg 92: 502-04 (2001).
Martanto et al., Transdermal Delivery of Insulin Using Microneedles In Vivo,Pharm Res 21: 947-52 (2004).
McAllister et al., Microfabricated Needles for Transdermal Delivery of Macromolecules and Nanoparticles: Fabrication Methods and Transport Studies, Proc Natl Acad Sci USA 100: 13755-60 (2003).
Park et al., Polymer Microneedles for Controlled Release Drug Delivery, Pharm Res 23: 1008-19 (2006).
Prausnitz et al., Current Status and Future Potential of Transdermal Drug Delivery, Nat Rev Drug Discov 3: 115-24 (2004).
Prausnitz et al., Microneedles for transdermal drug delivery, Adv Drug Deliv Rev 56: 581-87 (2004).
Prausnitz et al., Microneedles, Percutaneous Penetration Enhancers (Smithand & Maibach, eds.) 239-55, CRC Press, Boca Raton, FL (2005).
Bierwagen, Electrochim 37: 1471-78 (1992).
Chabri et al., Microfabricated silicon microneedles for nonviral cutaneous gene delivery, Br J Dermatol 150: 869-77 (2004).
Cormier et al., Transdermal delivery of desmopressin using a coated microneedle array patch system, J. Control Release 97: 503-11 (2004).
Lin et al., Transdermal Delivery of Antisense Oligonucleotides with Microprojection Patch (macroflux®) Technology, Pharm Res 18: 1789-93 (2001).
Matriano et al., Macroflux microprojection array patch technology: a new and efficient approach for intracutaneous immunization, Pharm Res 19: 63-70 (2002).
Mikszta et al., Microneedle-based Intradermal Delivery of the Anthrax Recombinant Protective Antigen Vaccine, Nat Med 8: 415-19 (2002).
Mikszta et al., Protective Immunization against Inhalational Anthrax: A Comparison of Minimally Invasive Delivery Platforms, J Infect Dis 191: 278-88 (2005).
Zahn et al., Microfabricated Polysilicon Microneedles for Minimally Invasive Biomedical Devices, Biomed Microdevices 2: 295-303 (2000).

* cited by examiner

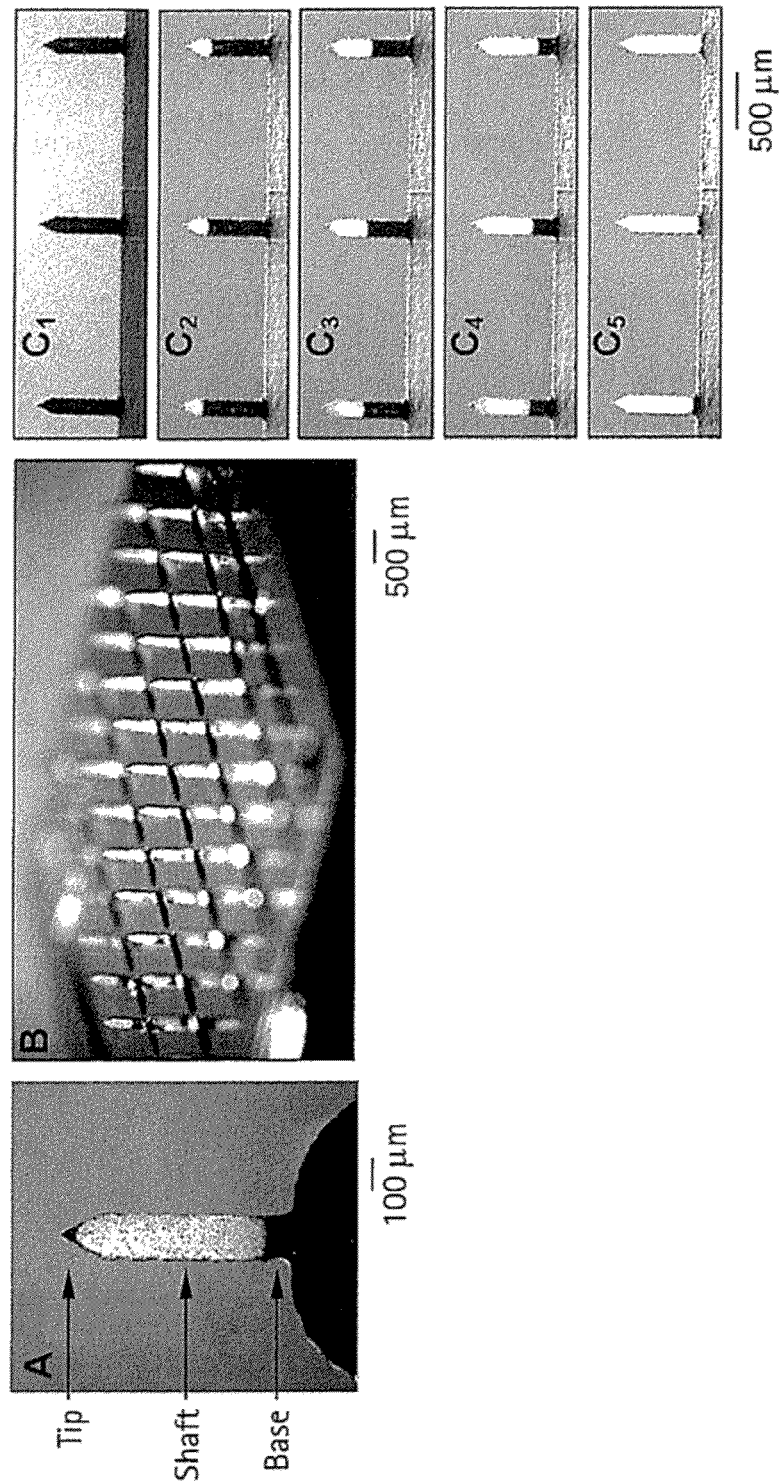

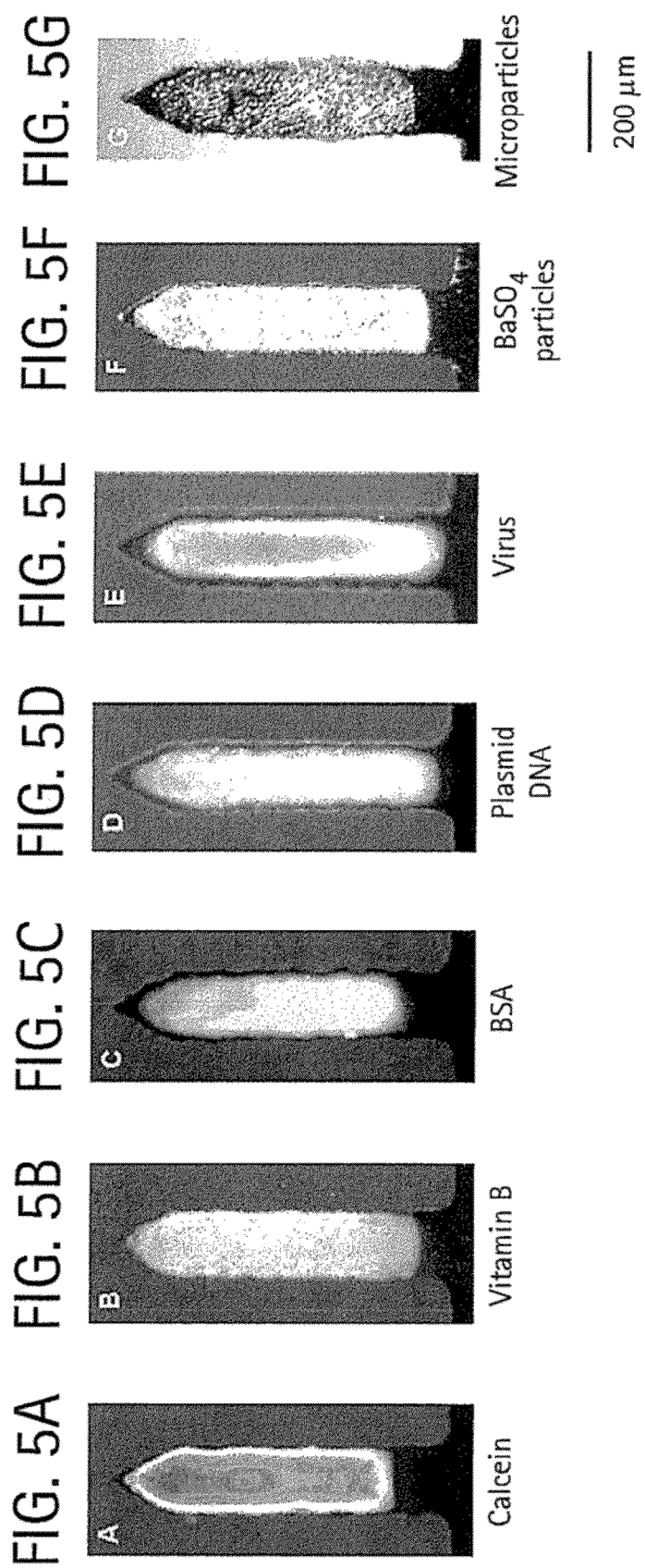

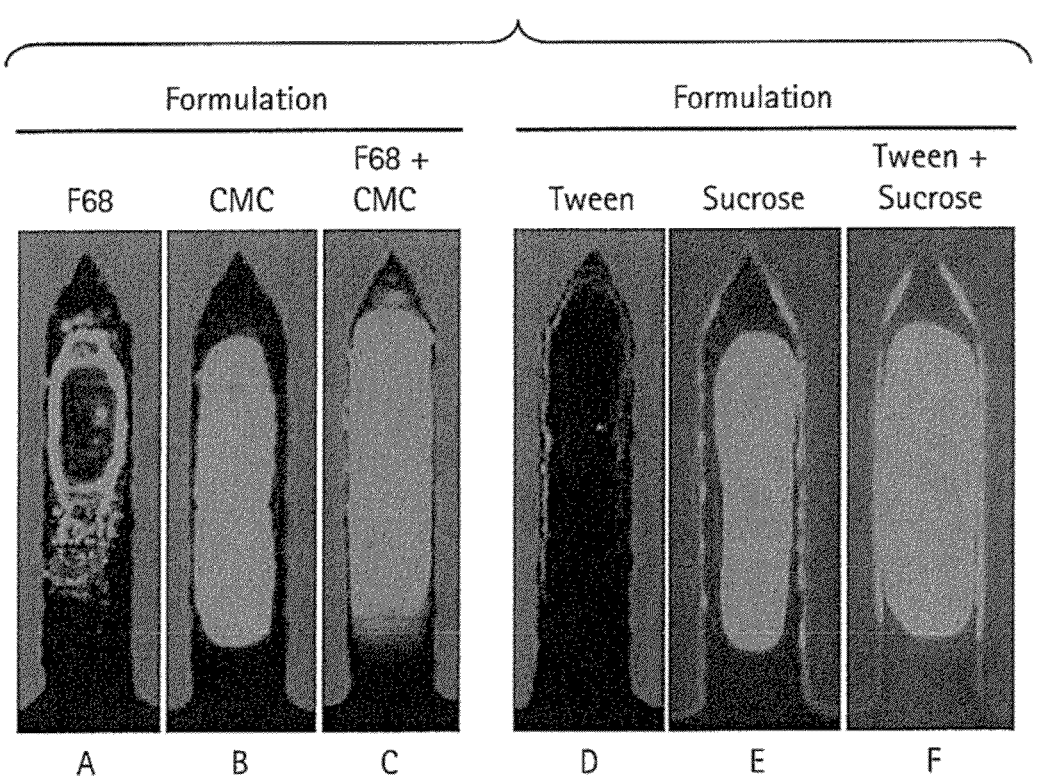

METHOD OF MAKING COATED MICROSTRUCTURES

CROSS REFERENCE TO RELATED APPLICATIONS

This application is a divisional of co-pending U.S. application Ser. No. 11/917,705, filed Dec. 14, 2007, which is a national phase of PCT/US2006/023814, filed Jun. 19, 2006. Priority to and benefit of U.S. Provisional Application No. 60/691,857, filed Jun. 17, 2005, and U.S. Provisional Application No. 60/732,267, filed Nov. 11, 2005, is claimed. The prior applications are incorporated herein by reference in their entirety.

STATEMENT REGARDING FEDERALLY SPONSORED RESEARCH OR DEVELOPMENT

This invention was made with U.S. government support under Contract No. 8 RO1 EB00260-03 awarded by the National Institute of Health. The U.S. government has certain rights in the invention.

BACKGROUND OF THE INVENTION

This invention is generally in the field of microneedles useful in medical applications, and more particularly to coated microneedles for drug delivery and sensing, such as transdermally.

Biopharmaceuticals, such as peptides, proteins, and future uses of DNA and RNA, represent a rapidly growing segment of pharmaceutical therapies (Walsh, *Trends Biotechnol* 23:553-58 (2005)). These drugs are delivered almost exclusively by the parenteral route, as the oral route is generally unavailable due to poor absorption, drug degradation, and low bioavailability. However, conventional parenteral administration with hypodermic needles undesirably requires expertise for delivery, can lead to accidental needle sticks, and causes pain, which results in reduced patient compliance. Given these problems, efforts have been made to develop alternate drug delivery routes to replace hypodermic needles (Orive et al., *Curr Opin Biotechnol* 14:659-64 (2003)). It would be desirable to provide drug delivery methods and devices that avoid the limitations and disadvantages associated with the use of conventional hypodermic needles.

Transdermal drug delivery is an especially attractive alternative to conventional hypodermic needles, because it is usually easy to use, safe, and painless (Prausnitz et al., *Nat Rev Drug Discov* 3:115-24 (2004)). The tough barrier posed by the skin's outer layer of stratum corneum has limited the applicability of this method to drugs that are hydrophobic, low molecular weight, and potent, as the stratum corneum's barrier properties severely limit passive delivery of most drugs, especially macromolecules and microparticles.

The use of micron-scale needles assembled on a transdermal patch has been proposed as a hybrid between hypodermic needles and transdermal patches that can overcome the problems of both injections and patches (Prausnitz et al., *Microneedles* In *Percutaneous Penetration Enhancers* (Smithand & Maibach, eds), pp. 239-55, CRC Press, Boca Raton, Fla., 2005)). Microneedles have been shown to be painless in human subjects relative to hypodermic needles (Mikszta et al., *Nat. Med.* 8:415-19 (2002); Kaushik et al., *Anesth Analg* 92:502-04 (2001). Unlike transdermal patches, microneedles also have been successfully used to deliver a variety of compounds into the skin, including macromolecules. In vitro skin permeability enhancement of two to four orders of magnitude has been observed for small molecules (e.g., calcein) and large compounds (e.g., proteins and nanoparticles) (Henry et al., *J Pharm Sci* 87:922-25 (1998); McAllister, et al., *Proc Natl Acad Sci USA* 100:13755-60 (2003)). In vivo delivery has been shown for peptides, such as insulin and desmopressin (Martanto et al., *Pharm. Res.* 21:947-52 (2004); Cormier, et al., *J Control Release* 97:503-11 (2004)); genetic material, including plasmid DNA and oligonucleotides (Lin et al., *Pharm. Res.* 18:1789-93 (2001); Chabri et al., *Br J Dermatol* 150:869-77 (2004)); and vaccines directed against hepatitis B and anthrax (Mikszta et al., *Nat. Med.* 8:415-19 (2002); Mikszta et al., *J Infect Dis* 191:278-88 (2005)).

Four different modes of microneedle-based drug delivery have been primarily investigated (Prausnitz, *Adv Drug Deliv Rev* 56:581-87 (2004); Prausnitz et al., *Microneedles* In *Percutaneous Penetration Enhancers* (Smithand & Maibach, eds), pp. 239-55, CRC Press, Boca Raton, Fla., 2005). These modes are (1) piercing an array of solid microneedles into the skin followed by application of a drug patch at the treated site (Henry, *J. Pharm. Sci.* 87:922-25 (1998)); (2) coating drug onto microneedles and inserting them into the skin for subsequent dissolution of the coated drug within the skin (Cormier et al., *J Control Release* 97:503-11 (2004)); (3) encapsulating drug within biodegradable, polymeric microneedles followed by insertion into skin for controlled drug release (J-H Park, et al., *Pharma. Res.* 23:1008-19 (2006)); and (4) injecting drug through hollow microneedles (Zahn et al., *Biomed Microdevices* 2:295-303 (2000)).

Among these approaches, coated microneedles are attractive for rapid bolus delivery of high molecular weight molecules into the skin, which can be implemented as a simple 'Band-Aid'-like system for self-administration. Furthermore, storing a drug in a solid phase coating on microneedles may enhance long-term stability of the drug, even at room temperature. For instance, desmopressin coated onto microneedles has been shown to maintain 98% integrity after six months storage under nitrogen at room temperature (Cormier et al., *J Control Release* 97:503-11 (2004)). Coated microneedles are also particularly attractive for vaccine delivery to the skin, because antigens can be targeted to epidermal Langerhans cells and dermal dendritic cells for a more potent immune response. For example, a strong immune response against a model ovalbumin antigen delivered from coated microneedles has been shown in guinea pigs (Matriano et al., *Pharm Res* 19:63-70 (2002)).

While the microneedle itself can be fabricated by adapting the tools of the microelectronics industry for inexpensive, mass production (Reed & Lye, *Proc IEEE* 92:56-75 (2004)), precise coating of microneedles presents technical challenges. Among the various conventional coating processes, such as dip coating, roll coating and spray coating (Bierwagen, *Electrochim.* 37:1471-78 (1992)), dip coating is particularly appealing for coating microneedles because of its apparent simplicity and ability to coat complex shapes. A conventional dip-coating process typically involves submerging and withdrawing an object from a coating solution, and then drying the continuous liquid film adhering to the surface of the object to yield a solid coating. However, such dip coating to coat microneedles by simply dipping and withdrawing them from an aqueous solution of a compound (e.g., calcein, sulforhodamine or vitamin B) results in non-uniform coatings with frequent spreading of the solution to the substrate from which the microneedles extend. Moreover, predictions of dip-coating theory to produce uniform coatings from different coating solutions mostly apply to static equilibrium systems; dynamic systems as in the case of dip coating are more complex. In addition, because surface tensiondriven phenomena often take place on the micron scale, conventional dip-coating methods have difficulty coating specified sections of micron-dimensioned structures, especially when those structures are closely spaced. For instance, bridging of liquid coating material between closely spaced microneedles is problematic. It therefore would be desirable to provide a micron-scale, dip coating process to coat microneedles with uniform and spatially controlled coatings using methods suitable for a breadth of drugs and biopharmaceuticals.

U.S. Pat. No. 6,855,372 to Trautman et al. discloses processes and apparatus for coating skin-piercing microprojections, in which dipping is done by moving the microprojections tangentially across and through a thin film of liquid on a rotating drum. Usefulness of the process would appear to be limited due to the tendency of ripple formation in the film while dipping microprojections. Ripples would cause liquid to touch and coat the substrate that carries the microprojections or would cause differences in coating length of microprojections on the leading and trailing edge of the array. The method also would appear be restricted to certain dip lengths and to certain microprojection spacings, given that wicking of liquid up between closely spaced microprojections and onto the base of the device would still be expected to be a problem. It therefore would be desirable to provide microneedle coating processes that reduces or eliminates between-needle wicking and offers better coating uniformity and better control of dip/coating length on each microneedle. It would also be desirable to provide improved methods for precisely coating microneedles or other microstructures with a variety of materials, including materials other than homogeneous liquid solutions.

SUMMARY OF THE INVENTION

Coated microneedle devices and methods of making such devices are provided. In one aspect, a method for coating includes providing a microstructure having at least one surface in need of coating; and applying a coating liquid, which comprises at least one drug, to the at least one surface of the microstructure, wherein the surface energy of the coating liquid is less than the surface energy of the surface of the microstructure. The method may further include precoating the at least one surface of the microstructure with a material to increase the surface energy of said surface, and/or modifying the coating liquid to decrease the surface tension of said coating liquid. The coating liquid may be aqueous, may include a viscosity enhancer and/or a surfactant. The method may include volatilizing at least a portion of a solvent, if used in the coating liquid, to form a solid coating. The coating liquid may comprises a molten material having a melting temperature greater than 25° C., which is then cooled to for a solid coating. In a preferred embodiment, the microstructure is a single microneedle or an array of two or more microneedles. In a preferred embodiment, a physical mask is utilized during application of the coating liquid to the microstructure.

In one embodiment, a method for coating at least one microneedle includes the steps of providing a coating liquid disposed in one or more reservoirs, the coating liquid comprising at least one drug; providing a physical mask having one or more apertures, each aperture having cross-sectional dimensions larger than the at least one microneedle to be coated; aligning the at least one microneedle with at least one of the one or more apertures; inserting the at least one microneedle through the aligned aperture and into the coating liquid, thereby coating at least a portion of the microneedle; and removing the coated microneedle from the coating liquid and from the aperture. The physical mask may include a plurality of holes or slits which closely circumscribe each microneedle or a single row of microneedles. The one or more reservoirs may be defined in a secondary structure, or the physical mask may have a plurality of the reservoirs defined therein. In one embodiment, the physical mask is in the form of a rigid plate secured to the reservoir. The coating liquid in the reservoir preferably is agitated or flowed to maintain composition uniformity.

In one embodiment, the step of inserting the microneedle through the aligned aperture is done before moving both the physical mask and the microneedle in a manner to cause the microneedle to be dipped into the coating liquid.

In another embodiment, the method further includes inserting the at least one microneedle into the same or a different coating liquid and then removing the microneedle from said same or different coating liquid.

In another aspect, a microneedle device for insertion of a drug into a biological tissue is provided that includes at least one microneedle having a base, a tip end, and a shaft portion therebetween; and a coating on at least a portion of the surface of the at least one microneedle, the coating comprising at least one drug and a viscosity enhancer. The coating may further include a surfactant. The viscosity enhancer may include cellulose, a cellulose derivative, hyaluronic acid, xanthan gum, alginic acid, alginic acid derivative, polyvinylpyrrolidone, acacia, guar gum, or a carbohydrate. The coating may have a heterogeneous composition, which may include discrete particles, two or more discrete layers, or two or more different phases. The coating may include a hydrogel, and the hydrogel coating may be in a dried state or hydrated state.

In one embodiment, all of the coating is adapted to come off of the microneedle following insertion into a biological tissue. For example, the coating may be adapted to come off of the microneedle in fifteen minutes or less following insertion into a biological tissue. In one case, the coating comprises drug dispersed in a matrix material which provides controlled release of the drug. In another case, the drug is a hydrophobic molecule and the coating further comprises an amphiphilic material.

In another embodiment, at least a portion of the coating is adapted to remain on the microneedle following insertion into a biological tissue. In still another embodiment, substantially all of the coating is adapted to remain on the microneedle, which may be a sensor, following insertion into a biological tissue.

In another aspect, a microneedle device is provided for insertion of a drug into a biological tissue, which includes at least one microneedle having a base, a tip end, and a shaft portion therebetween; and a coating on at least a portion of the surface of the at least one microneedle, the coating comprising at least one drug, wherein the coating has a heterogeneous composition. The coating may include discrete particles, two or more discrete layers, two different phases, or a combination thereof.

In another aspect, a microneedle device for insertion of a drug into a biological tissue is provided which includes at least one microneedle having a base, a tip end, and a shaft portion therebetween; and a coating on at least a portion of the surface of the at least one microneedle, the coating comprising at least one drug, wherein the shaft portion of the at least one microneedle comprises one or more pockets therein. The coating may be located substantially only in the one or more pockets. The one or more pockets may contain at least a portion of the coating where the coating is in the form of a liquid, gel, microparticles, or a combination thereof.

The at least one microneedle of these devices is formed of stainless steel, titanium, or another metal. In a preferred embodiment, the microneedles are electropolished. In preferred embodiments, the microneedle device includes two or more of the microneedles. The drug preferably is a therapeutic, diagnostic, or prophylactic agent.

In another aspect, a method is provided for making a microneedle device, which includes forming one or more microneedles from a metal; and electropolishing the one or more microneedles to smooth the surfaces of the microneedles. The step of forming may include laser cutting.

In still another aspect, a microneedle patch is provided which includes an array two or more microneedles extending out of plane from a substrate; and an adhesive material disposed between the two or more microneedles, the adhesive material comprising an adhesive suitable for removably securing the microneedle patch to a patient's skin. The adhesive material may include a double-sided adhesive tape. It may be a pressure sensitive adhesive. In another embodiment, the adhesive material results from application of a liquid adhesive material to the substrate.

BRIEF DESCRIPTION OF THE DRAWINGS

FIGS. 4A-4B show examples of microneedles having good coating results using brightfield microscopy using a vitamin B coating solution. FIG. 4C shows various embodiments of microneedles having different coating lengths.

FIGS. 5A-5G show a variety of molecules and particles coated onto certain embodiments of single microneedles as seen using fluorescence or brightfield microscopy.

FIGS. 6A-6F show the effect of the surface tension and viscosity of different coating formulations on microneedle coating uniformity.

DETAILED DESCRIPTION OF THE PREFERRED EMBODIMENTS

Figure 1A:
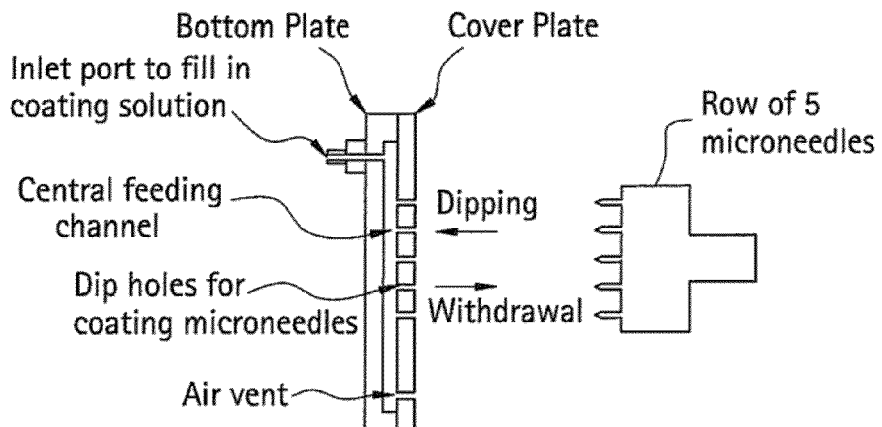
FIG. 1A is a cross-sectional view of one embodiment of an in-plane microneedle row-coating device showing the coating solution reservoir with the microneedle row aligned with the dip holes.

Coated microneedle devices and methods of coating microneedles have been developed to produce microneedles and microneedle arrays having a variety of coatings improvements, enabling a wide range of drug materials to be controllably coated onto microneedles and then delivered into biological tissues, particularly for transdermal drug delivery. The methods provide for uniform coatings, for coatings of particles or other heterogeneous coatings. The microneedle shafts may include pockets for containing coating materials, particularly liquid, gel, and particle coatings. In a preferred embodiment, the microneedle coating includes a solid coating that contains or consists of at least one drug. The coated microneedles may be incorporated into a transdermal drug delivery patch or other drug delivery device.

The coating process can reproducibly produce uniform, substantially continuous coatings on precise portions of the microneedles' shafts without bridging or patchiness, thereby providing enhanced dosage control in the manufacturing of drug coated microneedles. This is accomplished by various means of providing that the coating liquid precisely contacts the microneedle or selected portion thereof. In one embodiment, devices and methods have been developed to limit deposition of the coating to the microneedle. By avoiding deposition of the coatings onto the substrates having the microneedles, dosage control is improved and product loss during coating is minimized.

As used herein, the term "biological tissue" includes essentially any cells, tissue, or organs, including the skin or parts thereof, mucosal tissues, vascular tissues, lymphatic vessels, ocular tissues (e.g., cornea, conjunctiva, sclera), and cell membranes. The biological tissue can be in humans or other types of animals (particularly mammals), as well as in plants, insects, or other organisms, including bacteria, yeast, fungi, and embryos. Human skin and sclera are biological tissues of particular use with the present microneedle devices and methods of use thereof.

As used herein, the terms "comprise," "comprising," "include," and "including" are intended to be open, non-limiting terms, unless the contrary is expressly indicated.
Coated-Microneedle Devices In one aspect, a microneedle device is provided for insertion of a drug into a biological tissue. In a preferred embodiment, the device includes at least one microneedle having a base, a tip end, and a shaft portion therebetween, and a coating on at least a portion of the surface of the microneedle, wherein the coating comprises a drug and a viscosity enhancer.

In another aspect, a microneedle device is provided which includes at least one microneedle having a base, a tip end, and a shaft portion therebetween, and a coating on at least a portion of the surface of the microneedle, wherein the coating includes at least one drug and is a heterogeneous composition. For instance, the coating may have discrete particles, two or more discrete layers, two different phases, or a combination thereof. The drug may be in the particles, one or more of the layers, or one or more of the different phases.

In yet another aspect, a microneedle device is provided which includes at least one microneedle having a base, a tip end, and a shaft portion therebetween, and a coating on at least a portion of the surface of the microneedle, wherein the coating includes at least one drug and the shaft portion of the microneedle has one or more pockets therein.

Microneedles

The microneedle can be formed/constructed of different biocompatible materials, including metals, glasses, semiconductor materials, ceramics, or polymers. Examples of suitable metals include pharmaceutical grade stainless steel, gold, titanium, nickel, iron, tin, chromium, copper, and alloys thereof. In one embodiment, stainless steel is an attractive material for microneedle fabrication because it is FDA approved for medical devices and is inexpensive.

In another embodiment, the microneedle may include or be formed of a polymer. The polymer can be biodegradable or non-biodegradable. Examples of suitable biocompatible, biodegradable polymers include polylactides, polyglycolides, polylactide-co-glycolides (PLGA), polyanhydrides, polyorthoesters, polyetheresters, polycaprolactones, polyesteramides, poly(butyric acid), poly(valeric acid), polyurethanes and copolymers and blends thereof. Representative non-biodegradable polymers include polyacrylates, polymers of ethylene-vinyl acetates and other acyl substituted cellulose acetates, non-degradable polyurethanes, polystyrenes, polyvinyl chloride, polyvinyl fluoride, poly(vinyl imidazole), chlorosulphonate polyolefins, polyethylene oxide, blends and copolymers thereof. Biodegradable microneedles can provide an increased level of safety compared to non-biodegradable ones, such that they are essentially harmless even if inadvertently broken off into the biological tissue. This applies whether the microneedles contain molecules for delivery or serve merely as vehicle for transporting a drug coating.

In one embodiment, the microneedle device includes a substantially planar foundation from which one or more microneedles extend, typically in a direction normal (i.e., perpendicular or 'out-of-plane') to the foundation. Alternatively, microneedles may be fabricated on the edge of a substrate 'in-plane' with the substrate. In another embodiment, a single microneedle can be fabricated on a substrate surface or edge. In one embodiment, microneedles are fabricated on a flexible base substrate. It would be advantageous in some circumstances to have a base substrate that can bend to conform to the shape of the tissue surface. In another preferred embodiment, the microneedles are fabricated on a curved base substrate. The curvature of the base substrate typically would be designed to conform to the shape of the tissue surface.

The microneedles may be solid or hollow. The microneedles can be porous or non-porous. The microneedles may be planar, cylindrical, or conical. The microneedles can have a straight or tapered shaft. In one embodiment, the diameter of the microneedle is greatest at the base end of the microneedle and tapers to a point at the end distal the base. The microneedles can also be fabricated to have a shaft that includes both a straight (i.e., untapered) portion and a tapered portion. The microneedles can be formed with shafts that have a circular cross-section in the perpendicular, or the cross-section can be non-circular.

The tip portion of the microneedles can have a variety of configurations. The tip of the microneedle can be symmetrical or asymmetrical about the longitudinal axis of the shaft. The tips may be beveled, tapered, squared-off, or rounded. The tip portion generally has a length that is less than 50% of the total length of the microneedle.

The dimensions of the microneedle, or array thereof, are designed for the particular way in which it is to be used. The length typically is selected taking into account both the portion that would be inserted into the biological tissue and the (base) portion that would remain uninserted. The cross-section, or width, is tailored to provide, among other things, the mechanical strength to remain intact for the delivery of the drug or for serving as a conduit for the withdrawal of biological fluid, while being inserted into the skin, while remaining in place during its functional period, and while being removed (unless designed to break off, dissolve, or otherwise not be removed). In various embodiments, the microneedle may have a length of between about 50 µm and about 5000 µm, preferably between about 100 µm and about 1500 µm, and more preferably between about 200 µm and about 1000 µm. In one embodiment, the length of the microneedle is about 750 µm. In various embodiments, the base portion of the microneedle has a width or cross-sectional dimension between about 20 µm and about 500 µm, preferably between about 50 µm and about 350 µm, more preferably between about 100 µm and 250 µm. For a hollow microneedle, the outer diameter or width may be between about 50 µm and about 400 µm, with an aperture diameter of between about 5 µm and about 100 µm. The microneedle may be fabricated to have an aspect ratio (width:length) between about 1:1 and 1:10. Other lengths, widths, and aspect ratios are envisioned.

In a preferred embodiment, the microneedle includes one or more pockets. As used herein, the term "pocket" refers to an aperture extending crosswise into the microneedle shaft (e.g., perpendicular to the direction of microneedle movement during the process of insertion into biological tissue). The pocket preferably extends through the shaft, but it is envisioned that it alternatively may be closed at one end, distal the opening in the shaft. This is distinct from a hollow bore wherein a concentric space extends substantially through the axial length of the shaft. As used herein, the pockets are considered to be part of the surface of the microneedle. The pocket preferably contains coating material, which may be particularly advantageous in certain embodiments where the coating material needs to be protected from mechanical forces during the insertion process, e.g., when the coating comprises a liquid or particles. It has been found that such coating materials are more likely than others to be prematurely dislodged or wiped off of the microneedle during insertion into skin, diminishing the complete delivery of the complete dosage of the coating. However, the pockets of the microneedles advantageously function to shield the coating material therein from the mechanical forces of insertion. The pockets may be made in various shapes (e.g., circular, square, rectangular) and of various numbers and dimensions and different spacings within the microneedle.

In various embodiments, the microneedle device includes a single microneedle or an array of two or more microneedles. The microneedles can be fabricated as, or combined to form microneedle arrays. For example, the device may include an array of between 2 and 1000 (e.g., between 2 and 100) microneedles. In one embodiment, a device may include between 2 and 10 microneedles. An array of microneedles may include a mixture of different microneedles. For instance, an array may include microneedles having various lengths, base portion diameters, tip portion shapes, spacings between microneedles, drug coatings, etc.

Fabrication of Microneedles

The microneedle can be fabricated by a variety of methods known in the art or as described in the Examples below. Details of possible manufacturing techniques are described, for example, in U.S. Patent Application Publication No. 2006/0086689 A1 to Raju et al., U.S. Patent Application Publication No. 2006/0084942 to Kim et al., U.S. Patent Application Publication No. 2005/0209565 to Yuzhakov et al., U.S. Patent Application Publication No. 2002/0082543 A1 to Park et al., U.S. Pat. No. 6,334,856 to Allen et al., U.S. Pat. No. 6,611,707 to Prausnitz et al., U.S. Pat. No. 6,743,211 to Prausnitz et al., all of which are incorporated herein by reference.

In a preferred embodiment, the microneedles are cut from stainless steel or other metal sheets using a laser (e.g., an infrared laser) or other techniques known in the art. Microneedles of different lengths and widths from sheets up to 125 µm have been successfully fabricated by this method.

In a preferred embodiment, an electropolishing technique is used to produce clean, smooth, and sharp microneedle surfaces. Electropolishing can remove slag deposits from the microneedles, as laser-cutting of metals such as stainless steel may produce microneedles with rough edges covered with slag deposits. In one non-limiting embodiment, laser cut stainless steel microneedles can be electropolished in a solution that includes glycerin, ortho-phosphoric acid (85%), and water in a ratio of 6:3:1 by volume. In one example, a copper plate is used as the cathode and the metal microneedles serve as the anode. The anode may be vibrated using means known in the art to help remove gas bubbles generated at the anodic surface during electropolishing. Electropolishing is believed to be especially effective, because current density (i.e., etching rate) is largest at sites of high curvature, which inherently targets sites of surface roughness for removal. In some embodiments, the electropolishing process has an output rate of finished microneedle arrays of one 50-needle array every 30 minutes using a single laser. This rate can be increased by process optimization and use of multiple lasers.

Coating/Drug Formulation

The microneedles include at least one drug-containing coating over at least part of the surface of the microneedle. In a preferred embodiment, the coating is applied in a manner such that the surface energy (or surface tension) of the coating liquid is less than the surface energy of the microneedle. This facilitates effective coating of the microneedle. As detailed herein, this surface energy differential may be achieved by modifying the coating liquid, modifying the microneedle surface properties, or a combination of such modifications.

In one aspect, the microneedle coating may be a heterogeneous composition. For example, the coating may include two or more phases (e.g., solid/liquid, solid/solid, emulsion, gel) two or more discrete layers, discrete particles, or a combination thereof. In one embodiment, the microneedle includes one or more pockets which are coated to contain a drug formulation which is in the form of a liquid, gel, particles, or a combination thereof.

The coating may consist of only the one or more drugs or it may include one or more non-volatile components (i.e., the components remaining after the solvent of the coating liquid has been volatilized) to modify the surface energy properties of the coating, to modify release characteristics of the drug, or to do both. Components may also be added to improved adhesion of wet or dry coating to the microneedle. Such non-volatile components are described below in discussing the coating liquid.

In one embodiment, all of the coating is adapted to come off of the microneedle following insertion into a biological tissue. In a preferred embodiment, the coating is adapted to come off of the microneedle rapidly. Rapid dissolution is equal to or less than 15 minutes, preferably less than 5 minutes, more preferably less than 5 minutes, and more preferably less than 10 sec. This embodiment would be particularly useful to deliver vaccines, local anesthetics (e.g., lidocaine), cosmetic formulations (e.g., botox, tattoos), and drugs suitable for bolus delivery. In one case, the coating comprises drug dispersed in a matrix material (e.g., microencapsulated) which provides controlled release of the drug. In another case, the drug is a hydrophobic molecule and the coating further comprises an amphiphilic material, which facilitates dissolution/release of the coating from the microneedle.

In another embodiment, the coating is adapted for slow release (e.g., dissolution) when inserted into a biological tissue. Slow dissolution is more than 15 minutes, and may range, for example, from a few hours to a day or two, or a week. This embodiment would be particularly useful to deliver clonidine (e.g., to treat hypertension), testosterone (e.g., for replacement therapy), insulin (e.g., for basal diabetic therapy), and other drugs suitable for long-term therapy, particularly drugs with relatively narrow therapeutic windows. In still another embodiment, the coating comprises a material which is substantially insoluble when inserted into a biological tissue.

In one embodiment, at least a portion of the coating is adapted to remain on the microneedle following insertion into a biological tissue. For example, the coating may include a matrix material or layer that serves to modulate release of a drug, which may be dispersed therein, which may be located in an underlying layer, or both.

In still another embodiment, all or substantially all of the coating is adapted to remain on the microneedle following insertion into a biological tissue. For example, the microneedle may be part of a sensor, and the coating material may aid in operation of the sensor without being released.

In one embodiment, the coating may include a plurality of discrete microparticles or other particles. The coating may consist only of these particles, packed together to form a coating once the solvent of the coating liquid has been volatilized. Alternatively, these particles may be dispersed within a continuous matrix material. Examples of the particles or microparticles that may form part or all of the coating include solid or gel-like organic or inorganic compounds in a non-dissolving solvent (e.g., barium sulfate suspension in water), liposomes, proteins, cells, virus particles, prions, and combinations thereof. In one case, drug molecules are incorporated into a microparticle or nanoparticles form. As used herein, the term "microparticle" encompasses microspheres, microcapsules, microparticles, and beads, having a number average diameter of 1 to 100 µm, most preferably 1 to 25 µm. The term "nanoparticles" are particles having a number average diameter of 1 to 1000 nm. Microparticles may or may not be spherical in shape. "Microcapsules" are defined as microparticles having an outer shell surrounding a core of another material, in this case, drug. The core can be liquid, gel, solid, gas, or a combination thereof "Microspheres" can be solid spheres, can be porous and include a sponge-like or honeycomb structure formed by pores or voids in a matrix material or shell, or can include multiple discrete voids in a matrix material or shell. The microparticle or nanoparticles may further include a matrix material. The shell or matrix material may be a polymer, amino acid, saccharide, or other material known in the art of microencapsulation.

In another embodiment, the microneedle coating includes multiple, discrete (distinct) layers. This may be achieved, for example, by using multiple dipping and drying steps, into the same or different coating liquids.

In a preferred embodiment, the microneedle is first coated with a precoat material, which is disposed between at least a portion of the at least one microneedle and the coating which comprises the drug. Such a precoat material preferably is used to alter or improve the surface properties (e.g., hydrophilicity or hydrophobicity) of the microneedle surface to enhance adhesion and uniformity of the drug-containing coating. The use of a precoat may enable one to omit surfactant from the primary, drug-containing coating liquid. The precoat may be substantially soluble or insoluble in vivo. In non-limiting examples, the precoat may consist of silicon dioxide or a biocompatible polyester, polyethylene glycol (PEG), PLGA or polyanhydride. Deposition of silicon dioxide or other precoat material may be achieved using vapor deposition or other techniques known in the art.

In still other embodiments, an exterior, secondary coating may be used to alter release kinetics of a drug from an underlying coating layer. For example, the exterior coating may include a material known in the art that dissolves or biodegrades relatively solely in vivo to provide delayed or slow release of drug. In one example, the exterior coating could include a hydrogel or other water swellable material to provide controlled drug release. In another variation, an exterior layer could provide for rapid (e.g., bolus) release of drug. An underlying layer could provide bolus or controlled release of the same or another drug.

Optionally, additional drug can be integrated into the microneedle structure, passed through bores or channels in the microneedle, or a combination thereof.

A wide range of drugs may be formulated for delivery with the present microneedle devices and methods. As used herein, the terms "drug" or "drug formulation" are used broadly to refer to any prophylactic, therapeutic, or diagnostic agent, or other substance that may be suitable for introduction to biological tissues, including pharmaceutical excipients and substances for tattooing, cosmetics, and the like. The drug can be a substance having biological activity. The drug formulation may include various forms, such as liquids, liquid solutions, gels, hydrogels, solid particles (e.g., microparticles, nanoparticles), or combinations thereof. The drug may comprise small molecules, large (i.e., macro-) molecules, or a combination thereof. In a preferred embodiment, the drug formulation is solid at ambient temperatures so that the coating on the microneedle is solid. A solid coating may increase the shelf life of certain active agents and can provide better ease of handling of the coated microneedles.

In representative, non-limiting, embodiments, the drug can be selected from among amino acids, vaccines, antiviral agents, DNA/RNA, gene delivery vectors, interleukin inhibitors, immunomodulators, neurotropic factors, neuroprotective agents, antineoplastic agents, chemotherapeutic agents, polysaccharides, anti-coagulants, antibiotics, analgesic agents, anesthetics, antihistamines, anti-inflammatory agents, and vitamins. The drug may be selected from suitable proteins, peptides and fragments thereof, which can be naturally occurring, synthesized or recombinantly produced. In one embodiment, the drug formulation includes insulin.

A variety of other pharmaceutical agents known in the art may be formulated for administration via the microneedle devices described herein. Examples include β-adrenoceptor antagonists (e.g., carteolol, cetamolol, betaxolol, levobunolol, metipranolol, timolol), miotics (e.g., pilocarpine, carbachol, physostigmine), sympathomimetics (e.g., adrenaline, dipivefrine), carbonic anhydrase inhibitors (e.g., acetazolamide, dorzolamide), prostaglandins, anti-microbial compounds, including anti-bacterials and anti-fungals (e.g., chloramphenicol, chlortetracycline, ciprofloxacin, framycetin, fusidic acid, gentamicin, neomycin, norfloxacin, ofloxacin, polymyxin, propamidine, tetracycline, tobramycin, quinolines), anti-viral compounds (e.g., acyclovir, cidofovir, idoxuridine, interferons), aldose reductase inhibitors, anti-inflammatory and/or anti-allergy compounds (e.g., steroidal compounds such as betamethasone, clobetasone, dexamethasone, fluorometholone, hydrocortisone, prednisolone and non-steroidal compounds such as antazoline, bromfenac, diclofenac, indomethacin, lodoxamide, saprofen, sodium cromoglycate), local anesthetics (e.g., amethocaine, lignocaine, oxbuprocaine, proxymetacaine), cyclosporine, diclofenac, urogastrone and growth factors such as epidermal growth factor, mydriatics and cycloplegics, mitomycin C, and collagenase inhibitors.

Coating Methods

Methods have been developed for coating microneedles. It also is envisioned that the present coating methods and devices can be used or readily adapted to coat other microstructures, particularly structures having micron-scale dimensions where surface tension issues impact coating location, coating thickness, and coating processibility. Representative examples of other microstructures include microfluidic devices, microarrays, microelectrodes, AFM probes, microporous materials, microactuators, microsensors, and the like.

The Coating Liquid

The coating liquid is the material applied to coat the one or more microneedles. The coating liquid includes the coating/drug formulation material(s) described above that ultimately intended to serve as the microneedle coating. As used herein, the term "coating liquid" includes pure solutions, suspensions (e.g., solid particles-dispersed-in-liquid), emulsions, and combinations thereof, as well as molten materials. The molten material may be the active drug or it may act as the dissolving or suspending medium for the drug and/or additives or particles or a combination thereof. It is essentially any non-gas material or combination of materials having a viscosity suitable for use in a coating process to coat microneedles. The coating liquid may be homogeneous or heterogeneous. In a preferred embodiment, the coating liquid is aqueous. In one embodiment, the coating liquid comprises particles suspended in a solvent.

The surface energy (or surface tension) of the coating liquid preferably is less than the surface energy of the microneedle. Depending on the drug, and the solvent if any, the coating liquid may need to include one or more additives to alter the surface energy of the coating liquid. For example, the surface energy of stainless steel is 53.3 mN/m and the surface energy of water is 72.8 mN/m. Therefore, an aqueous coating solution may need to include one or more additives to reduce the surface tension of the coating solution to less than 53.3 mN/m—preferably while increasing the viscosity of the coating solution so that thicker rather than thin coatings will be formed.

Representative examples of additives include viscosity modifiers, surfactants, pH modifiers, diluents, or other pharmaceutically acceptable excipients known in the art. Such additives preferably are water soluble, FDA approved as injectable excipients (for safety), solid at room temperature (to convert into a solid phase upon drying), and possess high surfactant or viscosity enhancement activity per unit mass (to provide minimal usage of additives and thereby increase drug percentage in the dry coatings).

The coating liquid may include a solvent. As used herein, the term "solvent" is used generically and broadly to refer to any volatile component in the coating liquid, whether solvent or non-solvent for the drug in the coating liquid. The solvent is the component, if any, in the coating liquid that is volatilized (e.g., evaporates) during/following application of the coating liquid onto the microneedle, thereby causing the non-volatile coating materials to solidify and adhere to the microneedle. The solvent may be aqueous, organic, inorganic, or a combination thereof. Representative examples of the suitable solvents include water, ethanol, ethyl acetate, isopropanol, propylene glycol, and benzyl alcohol.

In a preferred embodiment, the coating liquid includes one or more surfactants in an amount/concentration effective to spread the coating liquid onto the microneedle and a viscosity enhancer in an amount/concentration effective to produce a coating having a desired thickness. For example, the thickness desired is determined, in part, by the dosage of drug needed per microneedle, the surface area of the microneedle expected to penetrate the biological tissue, and the number of microneedles per array. Examples of suitable surfactants include nonionic surfactants, such as Poloxamers (e.g., Lutrol F-68) and polyoxyethylene sorbitan fatty acid esters (e.g., Tween 20). Examples of suitable viscosity enhancers include cellulose and derivatives thereof (e.g., sodium salt of carboxymethylcellulose (low viscosity), hydroxylpropyl cellulose) hyaluronic acid, xanthan gum, alginic acid and derivatives thereof (e.g., sodium alginate, propylene glycol alginate), polyvinylpyrollidone, acacia, guar gum, or carbohydrates such as sucrose or maltose. The concentrations of these additives in the coating liquid may range from 0.1% to 70% (weight/volume %). In one embodiment, the coating liquid comprises a drug, 1% carboxymethylcellulose, an 0.5% Lutrol F-68 NF. It is understood, however, that the particular additives and concentrations chosen for each formulation will depend, in part, upon the coating requirements as well as any interaction among the particular drug and the additives selected.

Anionic, cationic or nonionic surfactants can be used. Representative examples and concentration ranges of anionic surfactants include docusate sodium (e.g., 0.01% to 1% wt/vol %) and sodium lauryl sulfate (e.g., 0.1% to 3% wt/vol %). A representative example and concentration range of a cationic surfactant includes benzalkonium chloride (e.g., 0.01% to 1% wt/vol %). Representative examples and concentration ranges of nonionic surfactants include polyoxyethylene sorbitan fatty acid esters (e.g., polysorbates 20, 40 and 60 at 0.1% to 3% wt/wt %), sorbitan fatty acid esters (0.1% to 3% wt/wt %), poloxamers (e.g. Lutrol F68 0.1% to 5% wt/vol %), and polyoxyethylene alkyl ethers (0.05% to 1% wt/vol %).

Certain drugs and certain coating liquids can be effectively and uniformly coated onto the microneedles without the need for surfactants or without the need for any additives. In one embodiment, certain hydrophobic drugs can be coated onto microneedles for quick release (e.g., between one and ten minutes) in vivo, where the coating liquid includes an amphiphilic viscosity enhancer without surfactant. Examples of suitable hydrophobic drugs include doxyrubicin, estradiol, testosterone, fentanyl, clonidine, oxybutynin, dexamethasone, indomethacin, and the like.

In one embodiment, the process is used where the surface energy of the coating liquid is less than the surface energy of the microneedle (either the material of construction or after surface modification). In an alternative embodiment, the coating liquid may have surface energy greater than the microneedle. This coating liquid will enable filling and coating of pockets in the microneedle surface without coating the remainder of the microneedle surface. The coating liquid may contain dissolved solid additives or drugs, or maybe devoid of any dissolved solids with even the drug being liquid at room temperature. In either case, the result will be a pocket filled with a solid (after drying) or a liquid phase, respectively. Particles may additionally be introduced into either of these formulations causing particles to be filled into the pockets. Relatively slow speeds of microneedle withdrawal, on the order of more than a second, from the microneedle immersed state to outside the coating liquid, have been found to be useful to facilitate the coating of only the pockets.

In another embodiment, the coating liquid is free of excipients all together. For instance, some drugs can remain stable at their melting point, and microneedles can be coated by dipping them into molten drug and then allowing the drug to cool and solidify, thereby forming the coating. In one embodiment, the coating liquid comprises a molten material having a melting temperature greater than 25° C. Such embodiments advantageously enable delivery of pure drug and provide high drug mass loading per microneedle. An example of a suitable drug for use in this coating method is lidocaine, clonidine, and the like.

Apart from molten liquid existing in a pure liquid state, multi-component molten coating also may be formulated. Multi-component molten coating liquids generally consist of a dissolving medium created by heating a solid above its melting point to form a liquid state, into which a drug is dissolved. For example, PEG (MW 1500) may be heated to 55° C. and then dexamethasone dissolved into it. The dissolving medium may be hydrophilic or hydrophobic. Representative examples of hydrophilic dissolving medium include to polyethylene glycols (PEGs) (melting point greater than 25° C.), sugars (especially low melting-point sugars such as xylitol (melting point 92-96° C.), dextrose (melting point 146-150° C.), maltose (melting point 102° C.), and sorbitol (melting point 110-112° C.), water soluble polyoxyethylene derivatives (e.g., Brijs, Brij 72, melting point 44-45° C.), polyethylene-propylene glycol copolymers (Poloxamers, e.g., Pluronic F-68, melting point 52° C.), poly(ethyleneoxide) (PEO) derivatives, PEG derivatives, PEG-PEO derivatives, or various combinations thereof. Representative examples of hydrophobic dissolving media include to glyceryl monostearate (melting point 55-60° C.), glyceryl palmitostearate (melting point 52-55° C.), cetyl alcohol (melting point 56° C.), stearyl alcohol (melting point 56-60° C.), bees wax (melting point 56-60° C.) and other wax and combinations thereof. Additives other than drugs may be included as dissolvable solids or liquid to the molten liquid coating solution to alter or improve the surface energy or viscosity of the molten coating liquid. Molten liquid coating liquids provide an alternative to solvent-based coating solutions to help satisfy surface energy or viscosity or other physicochemical properties required for a particular coating application.

Dip Coating Method and Apparatus

In one aspect, a method is provided for coating a microstructure, which method includes providing a microstructure having at least one surface in need of coating, and applying a coating liquid, which comprises at least one drug, to the at least one surface of the microstructure, wherein the surface energy of the coating liquid preferably is less than the surface energy of the surface of the microstructure. In one case, this method includes precoating the at least one surface of the microstructure with a material to increase the surface energy of said surface, or otherwise modifying the surface energy properties of the microneedle. In another case, the method includes modifying the coating liquid to decrease the surface tension of the coating liquid. In preferred embodiments, the microstructure comprises at least one microneedle.

In another aspect, a method is provided for coating at least one microneedle, which method includes the steps of (i) providing a coating liquid disposed in a reservoir, the coating liquid comprising at least one drug; (ii) providing a physical mask having one or more apertures therethrough, each aperture having cross-sectional dimensions larger than the at least one microneedle to be coated; (iii) aligning the at least one microneedle with at least one of the one or more apertures; (iv) inserting the at least one microneedle through the aligned aperture; (v) inserting the at least one microneedle into the coating liquid, thereby coating at least a portion of the microneedle; and (vi) removing the coated microneedle from the coating liquid and from the aperture. The one or more reservoirs may be defined in a secondary structure or the physical may have a plurality of the reservoirs defined in the physical mask.

Steps (iv) and (v) can be done in two discrete steps or in a single step. For example, the step of inserting the microneedle through the aligned aperture may be done before moving the physically masked microneedles to cause the microneedle to be dipped into the coating liquid; alternatively, the physical mask can be in a fixed position relative to the reservoir of coating liquid, so that only the microneedles are moved.

By utilization of a physical mask, access of the coating liquid is restricted only to the microneedle shaft, thereby preventing contamination of the substrate from which the microneedles extend. That is, any meniscus rise or capillary action that may cause contact of the coating liquid to an adjacent microneedle or with the substrate is advantageously avoided such that the coating is on a majority of the surface of the shaft and the base substrate is free of the coating. For example, in embodiments, the coating is on 50% to 100% of the surface of the microneedle or on 75% to 100% of the surface of the microneedle. Furthermore, this "micro-dip coating" process is particularly advantageous for use with relatively smaller coating liquid volumes, such as might the case when coating microneedles with highly potent or expensive substances, such as DNA/RNA.

In a preferred embodiment, the physical mask is in the form of a plate having a one or more discrete apertures therethrough. These apertures preferably are the form of one or more holes or slits which closely circumscribe each microneedle or a single row of microneedles. As used herein, the term "closely circumscribe" means that the physical mask is effective to restrain, by surface tension forces, the coating liquid to the reservoir and apertures, preventing it from "climbing up" the microneedle shaft substantially beyond the dipped portion of the microneedle which it is desired to coat. Surface energy properties of the coating system (physical mask, microneedle, and coating fluid) and operating conditions (e.g., temperature, dipping/withdrawal speed) impact the selection of appropriate dimensions for the holes and slits.

Figure 10A:
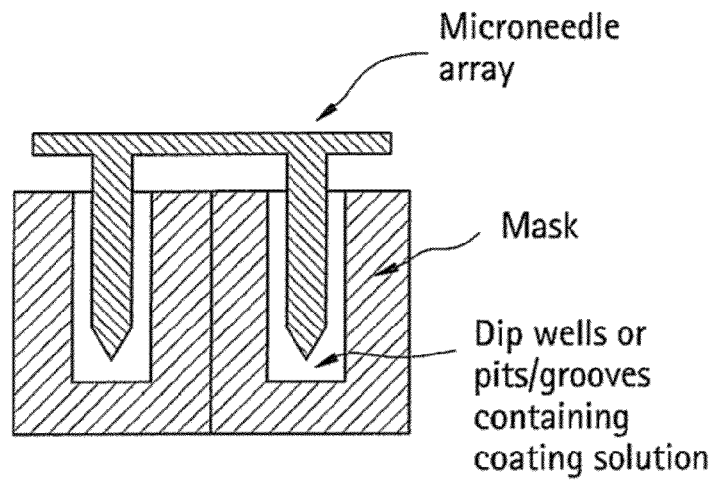
FIGS. 10A-10B are cross-sectional views of microneedles in a microneedle array which are dipped into a coating liquid using a physical mask to control deposition of coating, with mask having multiple closed dip holes built into the mask (FIG. 10A) or a single reservoir in fluid communication with open dip holes (FIG. 10B).

In one embodiment, the physical mask is in the form of a substantially rigid plate secured to the reservoir (see e.g., FIG. 10A). The plate includes an array of micron-sized holes corresponding to the microneedles in a microneedle array to be coated. When properly aligned, for example using micropositioners or pre-aligned parts moving on a rail, each of the microneedles can be simultaneously inserted through the micron sized holes and into the coating liquid, resulting in a controlled micro-dip-coating process. The use of one or more micropositioners can be used to provide control over the microneedle length being coated, that is how much of the microneedle length is actually coated. Physical stops in the form of think sheets or protruding cylinders in between the physical mask and microneedles may also be used to control the microneedle length being coated. The coating device can be configured to coat single microneedles, in-plane rows of microneedles (see, e.g., FIGS. 1A-B), and out-of-plane arrays of microneedles (see, e.g., FIG. 1C).

Figure 10B:
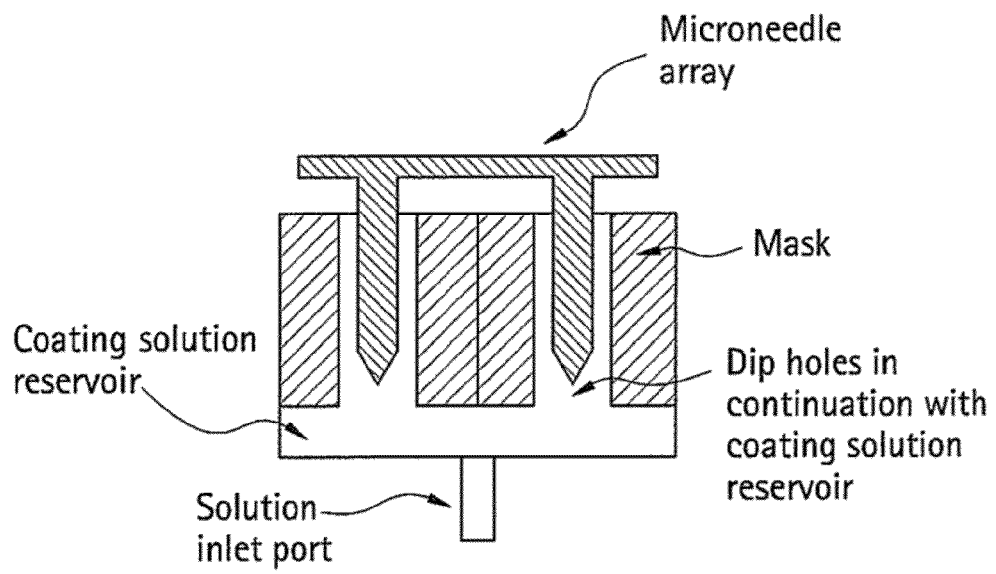

In another embodiment, the physical mask may be designed to act as a coating liquid reservoir or reservoirs. For instance, the physical mask may include reservoirs, closed at one end, that can be filled with the coating liquid (see, e.g., FIG. 10B). Single microneedles or multiple microneedles of an array can be dipped into each reservoir or groove. Typically, the apertures of the mask have a closed bottom, the coating liquid is filled in these apertures from the open top. These can be periodically or continually refilled to maintain a constant amount of coating liquid in the reservoir.

To reduce propensity of air bubbles in the reservoir and/or apertures in the plate, the device may include vent holes designed to release entrapped air. To prevent evaporation of coating liquid (or solvent thereof) from the coating liquid, a pumping device (e.g., an automated or manually pulsated syringe plunger) can be included with the coating apparatus to fill the coating liquid reservoir and to oscillate/mix the coating liquid in dip-coating holes. The coating liquid in the reservoir may be flowed or agitated to facilitate maintenance of a uniform coating liquid composition during the dipping process. Alternatively or in addition, the coating process may be performed at a reduced temperature (relative to ambient) to reduce the rate of evaporation of the coating liquid or solvent portion thereof.

In one embodiment, the method further includes the step of volatilizing at least a portion of the solvent to form a solid coating. This may be referred to as "drying" the coating or coating liquid. A similar step may be included when using molten coating liquids, wherein the coated liquid is permitted to (or actively caused to) cool the molten material sufficiently to cause it to solidify, forming a solid coating on at least a portion of the microneedle.

The coating method may further includes inserting the at least one microneedle into the same or a different coating liquid and then removing the microneedle from said same or different coating liquid. The composition of the coating liquid may include a solvent to dissolve part of the previous coating, if desired. In another embodiment, the method may further include the step of applying a second coating liquid onto the solid coating or onto a second surface of the microneedle in need of coating. The composition of the second coating liquid may include a second drug. Multiple such dippings into the same or a different coating liquid may be repeated.

The process optionally may include an intervening dip into a cleaning solvent, e.g., to thin or remove part of a prior coating layer. This may be useful to build complete coating structures, e.g., where one coating composition is located on one part of the microneedle (e.g., a first pocket) and a second coating composition is located on another part of the microneedle (e.g., a second pocket).

While the present coating method using a physical mask has been described as applied to coat microneedles, it is envisioned that the process could be used or readily adapted to coat other microprotrusion type structures in other microstructures.

Coating Process Considerations

Based on thermodynamics, to obtain uniform coatings on microneedle surfaces, generally the surface tension of the coating liquid should be lower than the surface energy of the microneedle surface material (material of construction or overcoat deposition). A slow (taking more than a second) or rapid (taking less than a second or more preferably less than a tenth of a second or more preferably less than a hundredth of a second) withdrawal of the microneedle from the immersed state to outside the coating liquid will provide a uniform coating on the microneedle. Addition of a viscosity enhancer will increase the coating thickness by increasing the film thickness of the entrained liquid during withdrawal. However, the requirement of coating liquid surface tension being lower than the microneedle material can be overcome by conducting the coating process at a rate faster than is needed to achieve thermodynamic equilibrium. For instance, by increasing the viscosity and withdrawing at a rapid speed, the microneedle will entrain a significant volume of the liquid on the surface. If the solvent then evaporates before the liquid film can contract to form an island in the middle of the microneedle surface, the solid coating will become uniformly deposited onto the microneedles. Another way to overcome the surface tension barrier to obtain uniform coatings is to use a non-aqueous solvent that has lower surface tension, possibly lower than the microneedle material. Similarly, while coating only the pockets, advantage can be made of the kinetic effect by utilizing a high surface energy liquid/solution that will not wet the microneedle surface but will fill the pockets. Again, the speed must be sufficiently slow so that liquid does not entrain on the surface, but only gets into the pockets.

One factor for liquid 'pocket' coatings is that the all of the liquid formulation must have sufficient viscosity and low vapor pressure so that it can remain in the pockets for a sufficient duration to permit packaging and storage (e.g., under inert atmosphere and overpressure conditions) to substantially prevent vaporization. In another embodiment, the liquid coating may contain dissolved solids, which again must be sufficient to form a continuous film once the volatile solvent has evaporated.

Microneedle Array Patches

The microneedle device may be in the form of a patch for application to the skin of a patient. The patch may include one, or more preferably an array of tens or hundreds of microneedles (e.g., between 50 and 500) and an adhesive component to secure the patch to the skin. The patches may be fabricated using either multiple linear rows of in-plane microneedles, individual arrays of out-of-plane microneedles, or combinations thereof.

The adhesive component may be in the form of a flexible or rigid substrate which includes a pressure sensitive adhesive as known in the art.

In one embodiment, the microneedles and adhesive component are configured such that the microneedles extend through apertures in the adhesive layer. Individual microneedles or subgroups of microneedles (e.g., rows) can extend through a single aperture. By having the adhesive surface adjacent the microneedles, the adhesive is able to better hold the microneedles down and to compensate for the recoiling-tendency of skin and/or a rigid substrate for out-of-plane microneedles.

Figure 8A:
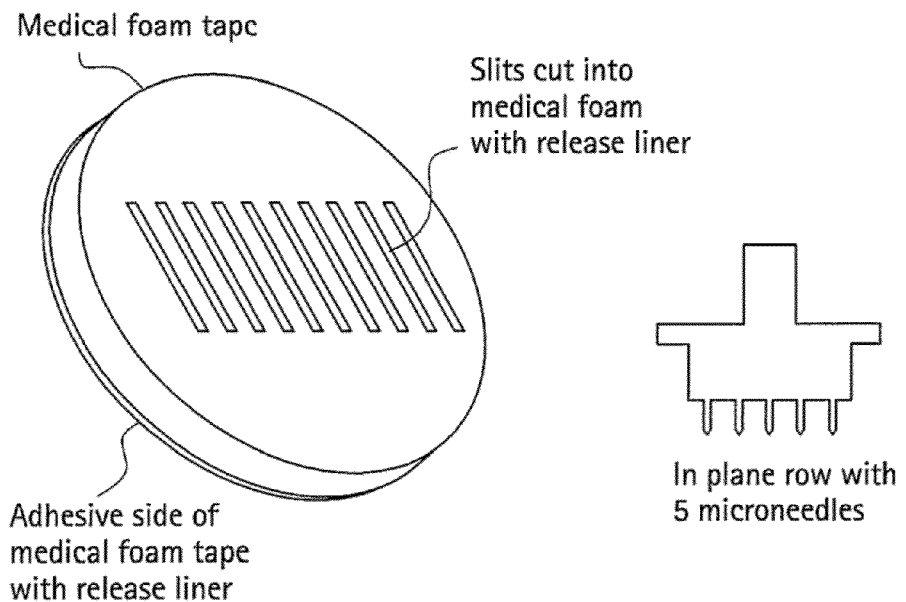
FIGS. 8A-8B illustrate one embodiment of a process for assembling a microneedle patch including coated in-plane microneedle rows as described herein.
Figure 8B:
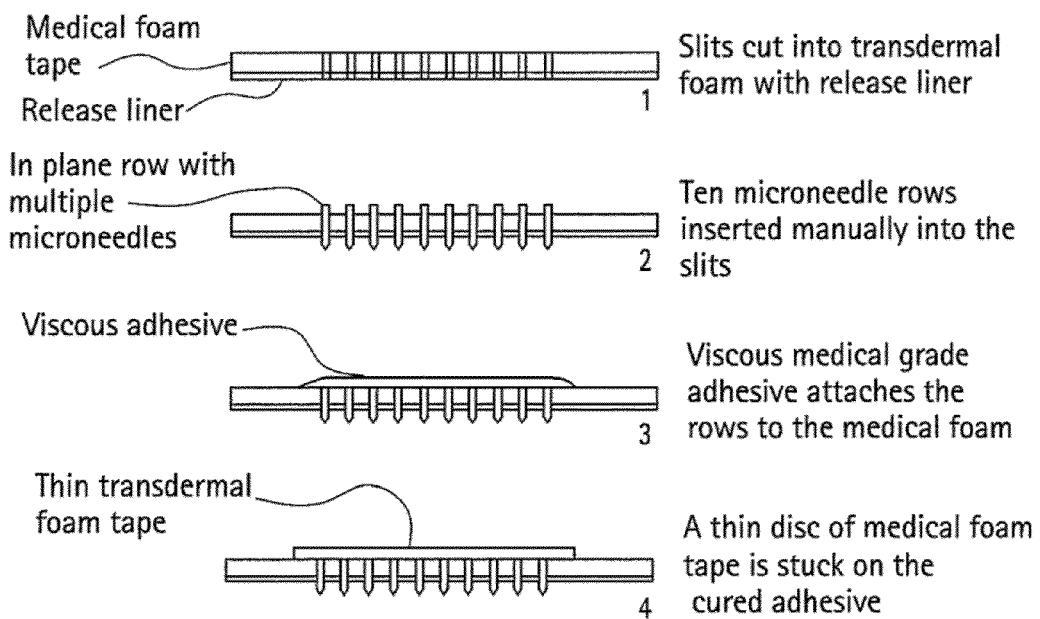

In one embodiment, in-plane microneedles are fabricated with a uniform adhesive layer in between the microneedles. For example, rows of microneedles can be assembled into a patch by forming slits (equal to the length of an in-plane row) in a material, such as polyethylene medical foam tape. Such cutting can be performed by any suitable technique, such as laser cutting. The microneedle rows can be manually inserted into each slit from the non-adhesive side of the foam tape and glued to the foam tape using a medical grade adhesive. The adhesive is then allowed to cure. Optionally, a polyethylene medical foam tape of sufficient thickness (e.g., 0.8 mm) can then be cut into a disc and affixed onto the dried glue area to provide a cushioned backing to facilitate pressing the patch during insertion. See FIG. 8.

Figure 9A:
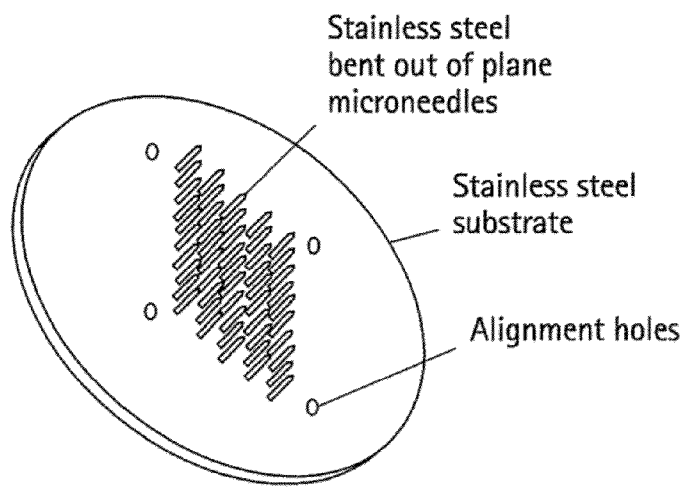
FIGS. 9A-9B illustrate another embodiment of a process for assembling a microneedle patch including coated out-of-plane microneedle arrays as described herein.
Figure 9B:
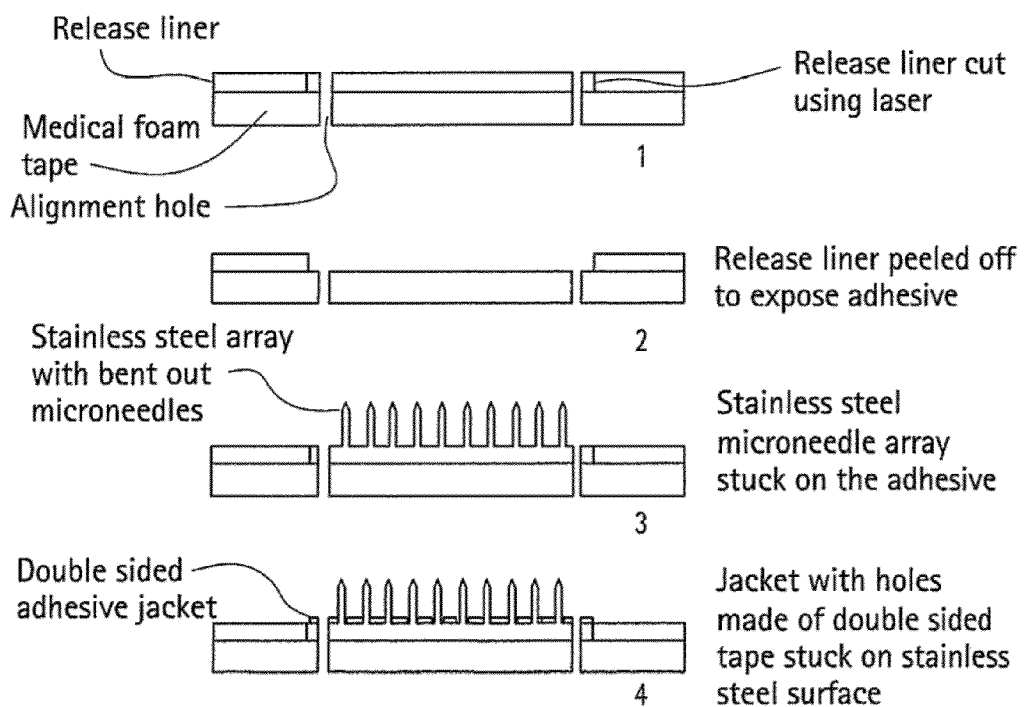

In another embodiment, a microneedle patch can be assembled using a complete microneedle array of out-of plane microneedles, a circular disc of a single-sided medical foam tape and a think double-sided medical tape. In the middle of the disc, a rectangular piece of adhesive release liner equal in dimensions to the periphery of the array can be cut out and peeled off. The stainless steel microneedle array can then be attached to this exposed adhesive. To provide a layer of pressure-sensitive adhesive on the stainless steel substrate of the affixed array itself, a double-sided, polyethylene terephthalate (PET) carrier tape first perforated with holes corresponding to the microneedles can be attached by slipping it over the microneedles using an alignment device. See FIG. 9.

The present coating methods and apparatus can be readily adapted for commercial production. For instances, automated systems are known, which can be used or readily adapted to sequentially grasp, position, dip, and release small parts, such as microneedles or microneedle arrays in an assembly-line fashion.

Uses of the Microneedle Devices and Patches

The microneedle devices described herein may be used to deliver substances into and through the various biological tissues. In a preferred application, the microneedle devices are used to deliver a drug, particularly a therapeutic, prophylactic, or diagnostic agent into the skin, sclera, or other biological tissue of a patient. As used herein, the term "patient" refers to a human, animal, or other living organism in need of therapeutic, diagnostic, or prophylactic intervention. In one embodiment, the drug formulation is one which undergoes a phase change upon administration. For instance, a solid drug formulation may be dissolved within tissue, where it then diffuses out for bolus or controlled release. In a preferred embodiment, the drug coating is highly soluble at the physiological pH of the patient to promote rapid delivery.

In one application, the coated microneedles are used for vaccination. For example, the drug can be targeted to Langerhans cells residing in the epidermis for a more potent immune response. Advantageously, the solid phase of the antigen in the coatings may help eliminate the cold-chain (storage/transportation) requirement, because the solid phase antigen may be more stable.

In one embodiment, the delivery of drug particles or drug-containing particles can be effectively delivered into a patient's skin using the present coated microneedles. Successful delivery of microparticles or other particles (e.g., up to 20 µm in diameter) may be enhanced by using insertion rates of at least 1 to 2 cm/s, by using microneedles with pockets, or a combination thereof. The dosage delivered may be controlled, for example, by controlling the size of the particles, the number of pockets per microneedle, the total number of microneedles, or a combination thereof.

The dissolution time maybe controlled from seconds to minutes to hours to days to weeks based on how the coating is formulated. In one example, the coating may be substantially insoluble and swell (e.g., hydrogels) to release the drug by diffusion. In another example, the coating may dissolve rapidly (e.g., in 10 to 20 seconds) after insertion in a patient's skin or sclera.

The amount of drug delivered within the tissue may be controlled, in part, by the type of microneedle used and how it is used. In a preferred embodiment, a coated microneedle is inserted into the biological tissue to allow the microneedle coating to dissolve and be delivered into a biological fluid. In a preferred embodiment, the microneedle is coated along a length equal to or less than the insertion depth so that no microneedle coating, and therefore no drug, is precluded from being delivered within the tissue.

The present methods for delivering a drug to a biological tissue include the step of inserting at least one coated microneedle into the biological tissue. The initial insertion depth of the microneedle may be between 200 µm and 5000 µm (e.g., more than 250 µm, 500 µm, 800 µm, or 1000 µm, and e.g., less than 4000 µm, 3000 µm, 2500 µm, 2000 µm, 1800 µm, or 1500 µm). In one embodiment, the insertion depth is between 200 and 1500 µm. As used herein, the terms "insertion depth" and the process of "inserting" the microneedle into biological tissue refer to the movement of the microneedle into the surface of the skin, and this depth includes both the distance the tissue is deformed (by the microneedle) and the distance the tissue is penetrated by the microneedle. The term "penetration depth" refers to the non-deformative incursion of the microneedle into the tissue. In other words, insertion depth equals penetration distance plus deformation distance under the tip of the microneedle.

There are various methods to control the insertion depth. In one embodiment, the microneedles are designed to have a length equal to the desired penetration depth. In another embodiment, the microneedles are designed to have a length longer than the desired penetration depth, but the microneedles are only inserted part way into the tissue. Partial insertion may be controlled by the mechanical properties of the tissue, which bends and dimples during the microneedle insertion process. In this way, as the microneedle is inserted into the tissue, its movement partially bends the tissue and partially penetrates into the tissue. By controlling the degree to which the tissue bends, the depth of microneedle penetration into the tissue can be controlled. In one embodiment, the microneedles are inserted into the tissue using a drilling or vibrating action. In this way, the microneedles can be inserted to a desired depth by, for example, drilling the microneedles a desired number of rotations, which corresponds to a desired depth into the tissue. See, e.g., U.S. Patent Application Publication No. 20050137525 A1 to Wang et al., which is incorporated herein by reference in its entirety.

In another embodiment, the microneedle insertion depth may be controlled by mechanical means. For example, the insertion of a longer microneedle may be physically limited to insert only up to a pre-specified length by encasing the microneedle (or microneedles or array) in a sheath with only part of the microneedle protruding out for tissue insertion. Alternatively, the microneedle or array may be secured onto a micropositioner which can control the depth of tissue insertion. The depth of insertion also may be controlled by the geometry of the microneedle, such as a widening of the needle, by the speed of insertion, where more rapid insertion generally results in deeper insertion depth, and/or by controlling skin mechanics, e.g., by stretching the skin which generally facilitates deeper insertion.

The microneedles may be vibrated following insertion or during retraction to facilitate separation of the coating from the microneedle.

In various embodiments, the methods may be adapted to deliver the drug formulation specifically to the epidermis, dermis, or subcutaneous tissue. The method may include essentially any means known for controlling deformation of the biological barrier during the microneedle insertion process. For instance, deformation of the biological tissue may be intentionally reduced by performing the insertion step with control of microneedle velocity, microneedle vibration, microneedle rotation, tissue stretching, or a combination thereof.

The microneedle devices also may be adapted to use the one or more microneedles as a sensor to detect analytes, electrical activity, and optical or other signals. The sensor may include sensors of pressure, temperature, chemicals, and/or electromagnetic fields (e.g., light). Biosensors can be located on the microneedle surface, inside a hollow or porous microneedle, or inside a device in communication with the body tissue via the microneedle (solid, hollow, or porous). The microneedle biosensor can be any of the four classes of principal transducers: potentiometric, amperometric, optical, and physiochemical. In one embodiment, a microneedle is coated with a drug formulation that has a sensing functionality associated with it. In an application for sensing based on binding to a substrate or reaction mediated by an enzyme, the substrate or enzyme can be immobilized on at least a portion of the surface of the microneedle. In another embodiment, a wave guide can be incorporated into the microneedle device to direct light to a specific location, or for detection, for example, using means such as a pH dye for color evaluation. Similarly, heat, electricity, light or other energy forms may be precisely transmitted to directly stimulate, damage, or heal a specific tissue or for diagnostic purposes. In one example, the microneedle coating may release a diagnostic agent and the microneedle detects a reaction product following reaction of the diagnostic agent with an analyte in vivo. In another example, the microneedle may be dual functional, delivering a drug via the coating and serving as a sensor not directly related to the drug delivered.

The present invention may be further understood with reference to the following non-limiting examples.

EXAMPLE 1

Fabrication of Coated Microneedles

Metal microneedles were laser cut, electropolished, and then coated with various coating materials. Coated single microneedles and coated microneedle arrays were produced.

Forming the Microneedle Structures

Solid microneedles were cut from stainless steel sheets (Trinity Brand Industries, SS 304, 75 µm thick; McMaster-Carr, Atlanta, Ga., USA) using an infrared laser (Resonetics Maestro, Nashua, N.H., USA), guided by CAD/CAM design, using techniques known in the art. Microneedles were prepared as single microneedles, individual rows of microneedles, or as two-dimensional arrays of microneedles.

Figure 3A:
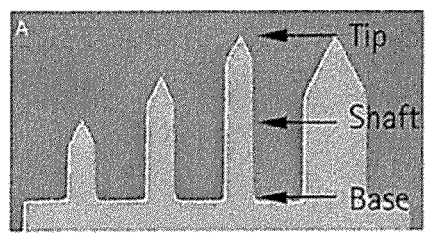
FIGS. 3A-3D are scanning electron microscope images showing different microneedle geometries including different lengths and widths with a tip angle of 55°, pockets of different shapes and sizes in microneedles, and different grooved surfaces, respectively in FIGS. 3A-C, and an out-of-plane array (FIG. 3D).
Figure 3B:
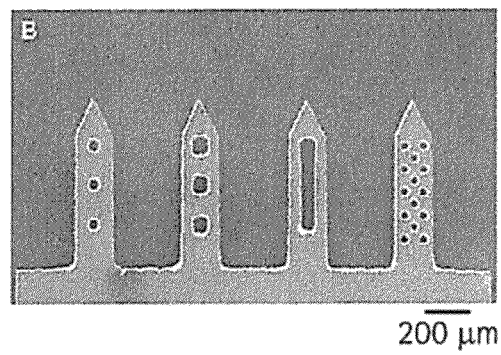
Figure 3C:
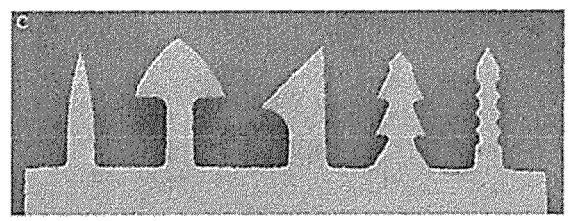
Figure 3D:
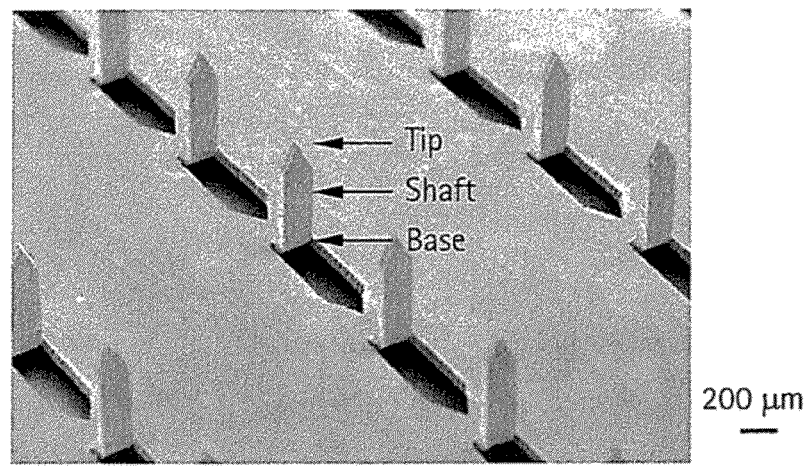

Microneedles were also made with a variety of shapes in increasingly complex geometries using laser etching. First, microneedles of different lengths and widths with a constant tip angle of 55° were created (FIG. 3A). Next, microneedles were made with small through-holes (i.e., "pockets") of different shapes and sizes in the shafts of the microneedles (FIG. 3B). Microscopic examination showed that the inside surfaces of these pockets were smooth and clean. Microneedles with grooved surfaces in the form of valleys and ridges were also made. Different patterns of valleys were successfully fabricated with uniform cleanliness and smoothness (FIG. 3C). The out-of-plane microneedles were prepared by manually pushing out at a 90° angle the microneedles that had been cut into stainless steel sheets (FIG. 3D).

Electropolishing

Figure 2A:
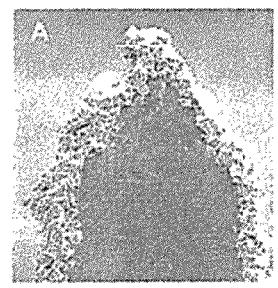
FIGS. 2A-2B show one embodiment of individual microneedles imaged by a scanning electron microscope after cleaning with powdered detergent and after electropolishing, respectively.
Figure 2B:
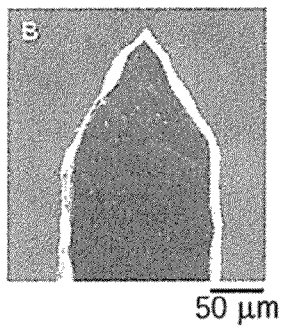

Because laser-cutting stainless steel produced microneedles with rough edges covered with slag deposits (FIG. 2A), an electropolishing technique was used to remove slag from the microneedles. The microneedles were electropolished in a solution containing glycerin, ortho-phosphoric acid (85%) and water in a ratio of 6:3:1 by volume (Fisher Chemicals, Fair Lawn, N.J., USA). A copper plate was used as the cathode, while the microneedles served as the anode. The anode was vibrated at a frequency of 10 Hz throughout the electropolishing process (current density of 1.8 mA/mm$^2$) using a custom built vibrating device to help remove gas bubbles generated at the anodic surface during electropolishing. The electropolishing process yielded microneedles with smooth surfaces and sharp tips (tip radius 0.5 to 1 µm) (FIG. 2B). The electropolishing process reduced the thickness of the microneedles to 50 µm.

Microneedle Coating

The electropolished microneedles were then coated with different molecules using a custom micron-scale, dip-coating process and specially formulated coating solutions. The micro-dip-coating devices and methods were used to localize coatings to only microneedle shafts for both single microneedles (FIG. 4A) and microneedle arrays (FIG. 4B).

Single microneedles were dip-coated by horizontally dipping the microneedle into 20-30 µl of coating solution held as a droplet on the tip of a 200 µl large-orifice pipette tip (Catalogue #21-197-2A, Fisher Scientific). The large-orifice pipette tip was mounted horizontally in a clamp and the microneedle was mounted opposite to it on a manual linear micropositioner (A1506K1-S1.5 Unislide, Velmex, Bloomfield, N.Y., USA). Immersion and withdrawal of the microneedle into the liquid droplet was performed manually by moving the microneedle while viewing under a stereomicroscope (SZX12, Olympus America).

Linear rows of microneedles were dip coated using a custom designed coating device, which included a coating solution reservoir and a micropositioning dip coater. As illustrated in FIG. 1A, the coating-solution reservoir of the micro-dip coating device consisted of two laminated parts: a 'bottom plate' and a 'cover plate', both of which were made of polymethylmethacrylate (McMaster-Carr). The two plates (bottom and cover plates) were aligned and adhered to each other using methylene chloride solvent bonding. The bottom plate had a central feeding channel (1 mm deep×0.5 mm wide) machined into one of its faces, with a through-hole drilled across to the other face, which acted as the inlet port to fill the channel with coating solution. The cover plate had five holes (400 µm diameter) drilled with the same spacing as the microneedles in the linear microneedle row. These "dip-holes" acted as individual dipping reservoirs to coat each of the microneedles in the row.

Figure 1B:
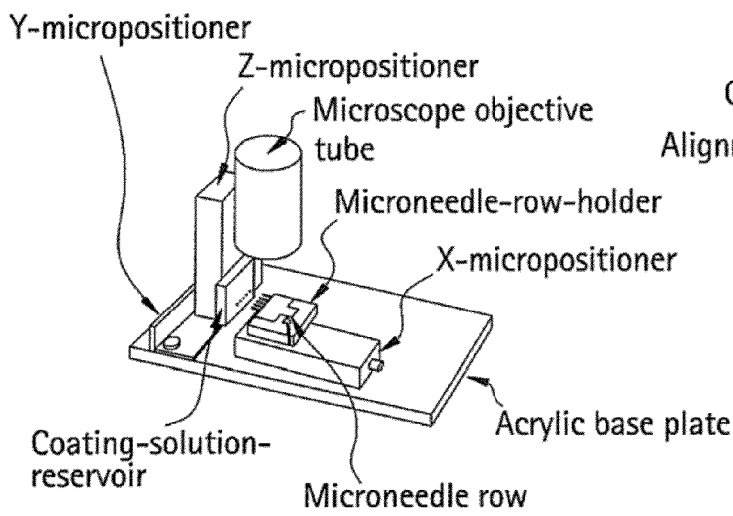
FIG. 1B is a perspective view of the in-plane microneedle row-coating device having x, y and z-micropositioners and a stereomicroscope objective. One embodiment of a coating device for coating an array of microneedles is shown in FIGS. 1C-1E, which includes a first portion (FIG. 1C) that includes a rectangular etched channel to hold coating solution, a feeding port, and alignment holes, and a second portion (FIG. 1D) that includes a physical mask with dip holes apertures and alignment holes.
Figure 1C:
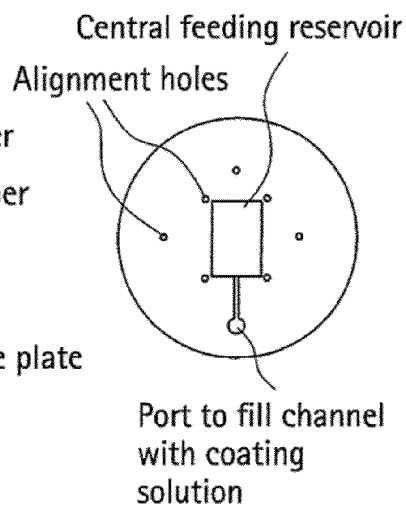
FIG. 1E shows a plan view of the two portions assembled.
Figure 1D:
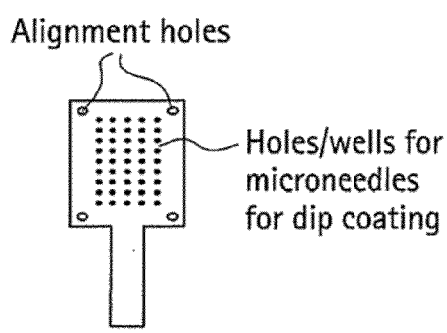
Figure 1E:
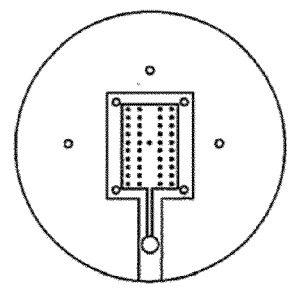

To enable three-dimensional alignment and dipping of microneedle rows into the dip-holes, three linear-micropositioners were assembled on a flat acrylic plate (FIG. 1B). The first micropositioner (x-micropositioner: A1503K1-S1.5 Unislide, Velmex) was used to position the linear microneedle array. The other two micropositioners were assembled stacked on one another on the acrylic plate to create a composite y-z motion micropositioner (two A1503K1-S1.5 Unislides, Velmex) that positioned the coating solution reservoir. Together, the three micropositioners permitted the alignment of the linear microneedle array to the dip-holes. The x-micropositioner was used to horizontally move the microneedles into and out of the dip-holes. The coating process was performed manually while viewing under a stereomicroscope (SZX12, Olympus). Control over the coating length on the microneedle shaft was exercised manually using the x-micropositioner. Tolerance for misalignment was included by designing the dip-hole diameter to be twice the width of the microneedles. Five in-plane microneedles containing five microneedles each were coated to predetermined lengths of 30%, 50%, 75% and 100% length coverage (FIGS. $4C_1$ to $4C_5$).

Microneedle arrays were dip-coated using a method and dipping device similar to that used to coat linear rows of microneedles. The coating-solution reservoir and the microneedle-array holder were pre-aligned opposite to each other on a vertical rod. The cover plate of the coating-solution reservoir contained 50 dip-holes at the same spacing as the microneedles in the array. The coating-solution reservoir was stationary, while the microneedle-array holder could be slid up and down the rod. Pins were provided on the microneedle-array holder to position a microneedle array on the holder in alignment with the dip-holes, and held in place using a magnet. To coat the microneedles, the microneedle-array holder was manually slid down the rod to dip the microneedles of the array into the 50 dip-holes below.

The coating solution included 1% (weight/volume %) carboxymethylcellulose sodium salt (low viscosity, USP grade, CarboMer, San Diego, Calif., USA), 0.5% (weight/volume %)) Lutrol F-68 NF (BASF, Mt. Olive, N.J., USA), and a model drug. The surface tension and viscosity of the coating solutions were modified with additives in order to deposit (more) uniform coatings on the microneedles. The model drugs tested included 0.01% sulforhodamine (Molecular Probes, Eugene, Oreg.), 0.01% calcein (Sigma, St. Louis, Mo., USA), 3% vitamin B (Fisher Chemicals), 1% bovine serum albumin conjugated to Texas Red (Molecular Probes), 0.05% gWiz™ luciferase plasmid DNA (6732 base pairs, Aldevron, Fargo, N. Dak., USA), $2 \times 10^9$ plaque forming units per ml of modified vaccinia virus—Ankara (Emory University Vaccine Center, Atlanta, Ga., USA), 10% barium sulfate (1 µm diameter particles, Fisher Chemicals), 1.2% 10-µm diameter latex beads (PN 6602796, Beckman Coulter, Miami, Fla., USA) and 8.2% 20-µm diameter latex beads (PN 6602798, Beckman Coulter), all w/v %. DNA and virus were made fluorescent by incubating with YOYO-1 (Molecular Probes) at a dye:base pair/virus ratio of 1:5 for 1 h at room temperature in the dark. These drug materials selected for coating ranged in size from small molecules (calcein-0.6 nm) to larger microparticles (20 µm latex beads) and included inorganic materials (barium sulfate), organic materials (latex), and materials of biological origin (protein-bovine serum albumin, plasmid DNA-luciferase plasmid, and virus-modified vaccinia). All were reproducibly coated onto the microneedles, with coatings uniform across the entire microneedle length (representative images, FIG. 5).

EXAMPLE 2

Assembly of Coated Microneedle Patches

Coated microneedle arrays, made as in Example 1, were assembled into transdermal patches containing pressure-sensitive adhesive to adhere to the skin. To secure microneedles in the skin at all times until ready to be removed, microneedles were integrated into a Band-Aid-like patch. This patch had pressure-sensitive adhesive on one complete side, with microneedles protruding therefrom. The adhesive secured the microneedles and compensated for the recoiling tendency of the skin and the rigid stainless steel substrate of out-of-plane microneedles. These patches were fabricated using either multiple linear rows of in-plane microneedles or individual arrays of out-of-plane microneedles.

Microneedle Patches Using Multiple Rows of Microneedles

In-plane microneedles were fabricated with a uniform adhesive layer in between the microneedles. In this example, a set of ten rows of microneedles, containing five microneedles each, was assembled into a patch of 50 microneedles. First, ten slits, each 75 µm wide and 7.7 mm long (i.e., equal to the length of an in-plane row) were laser cut into a 1.6 mm-thick, single-sided polyethylene medical foam tape (TM9716, MACtac, Stow, Ohio) using a $CO_2$ laser (LS500XL, New Hermes, Duluth, Ga., USA). The ten microneedle rows were then manually inserted into each slit from the non-adhesive side of the foam tape and glued to the foam tape using a medical grade adhesive (Loctite 4541, Rocky Hill, Conn., USA). The adhesive was allowed to cure for 24 hours. A polyethylene medical foam tape (0.8 mm thick; TM9942, MACtac) was then cut into a disc of 16 mm diameter and affixed onto the dried glue area to provide a cushioned backing to facilitate pressing the patch during insertion.

Microneedle Patches Using Complete Microneedle Arrays

To assemble a microneedle patch using a complete microneedle array of out-of plane microneedles, a circular disc of 20 mm diameter was first cut from a 0.8 mm-thick, single-sided medical foam tape (TM9942, MACtac) using a $CO_2$ laser. In the middle of this disc, a rectangular piece of the adhesive release liner equal in dimensions to the periphery of the array (i.e., 12 mm×12 mm) was cut out using the $CO_2$ laser and peeled off. The stainless steel microneedle array was then attached to this exposed adhesive. To provide a layer of pressure-sensitive adhesive on the stainless steel substrate of the affixed array itself, a double-sided, polyethylene terephthalate (PET) carrier tape (63.5 µm thick; T04314A, MACtac) was attached as follows. The PET film was first perforated with holes of 400 µm diameter at the same spacing as the microneedles using a $CO_2$ laser. The tape was then slipped over the microneedles using a custom-built alignment device and pressed to stick against the stainless steel substrate.

EXAMPLE 3

In vitro Dissolution of Microneedle Coating

To assess the in vitro dissolution time, single microneedles (n=3) coated with vitamin B, calcein, or sulforhodamine, made as in Example 1, were inserted into pig cadaver skin for 10 s or 20 s. Upon removal, these microneedles were imaged by fluorescence microscopy to detect residual coating. After 10 s insertion, a majority of the coating was dissolved. After 20 s insertion, the microneedle coating was completely dissolved. A sulforhodamine-coated microneedle showed similar dissolution and release into skin.

EXAMPLE 4

Delivery of Molecules and Particles by Coated Microneedles

Delivery from Individual Microneedles In Vitro

To further determine if the drug materials coated on the microneedles are actually delivered into the skin, single microneedles (n=3) coated with calcein or sulforhodamine, made as in Example 1, were inserted into pig cadaver skin for 20 s and removed. After removing the microneedles, fluorescence micrographs of coated microneedles and histological skin sections were collected using an Olympus IX70 fluorescent microscope with a CCD camera (RT Slider, Diagnostic Instruments). Brightfield micrographs were collected using an Olympus SZX12 stereomicroscope with a CCD camera (Leica DC 300, Leica Microsystems, Bannockburn, Ill., USA). Histological examination of pig cadaver skin was conducted on frozen sections. Pig cadaver skin was pierced with microneedles for 20 s, frozen in OCT compound (Tissue-Tek, 4583, Sakura Finetek, Torrance, Calif., USA), and cut into 10 µm-thick sections using a cryostat (Cryo-Star HM 560MV, Microm, Waldorf, Germany).

No residue was observed on the skin after insertion, and examination of histology sections of the pig skin revealed distribution of calcein along the periphery of the insertion point. Similar results were also observed for sulforhodamine, suggesting that the results are generally applicable to different molecules.

Delivery of Microparticles

For particle delivery assessment, single microneedles coated with barium sulfate particles (1 µm diameter, as measured by scanning electron microscopy), or latex beads (10 or 20 µm diameter), made as in Example 1, were inserted into pig cadaver skin for 1 min (n=3 microneedles for each insertion). After removing the microneedles, micrographs of coated microneedles and histological skin sections were collected. Digital X-ray imaging to detect barium sulfate was done using a Faxitron MX20 cabinet X-ray (Faxitron X-Ray, Wheeling, Ill., USA).

At a slow speed of approximately 0.5 to 1 mm/s, barium sulfate particles were delivered into pig skin without wiping-off on the surface, while latex beads 10 and 20 µm in diameter were wiped off on the skin surface. At a higher insertion speed of approximately 1 to 2 cm/s, the momentum of the microneedles was able to carry the 10 µm diameter beads coated on microneedles into the skin. However, the 20 µm diameter beads were still found as residue on the skin surface. The 20 µm diameter latex beads were delivered into the skin after loading them into the hollow protective cavity of the 'pockets' (400 µm long×50 µm wide×50 µm deep) and delivering at 1 to 2 cm/s. Delivery of microparticles into the skin from particle-coated microneedles was achieved.

EXAMPLE 5

In vivo and In vitro Insertion of Microneedle Arrays into Human Skin

For in vitro testing, out-of-plane microneedle arrays (n=3) were coated and assembled into patches as in Example 2, and then manually inserted into human cadaver skin for 1 min. After 1 min, the patch was removed and visually examined by brightfield microscopy to qualitatively assess the amount of residual coating left on the microneedles. The human cadaver skin was also imaged by brightfield microscopy to assess release and delivery of coatings into the skin. Visual examination of the coated patch after insertion into the skin in vitro showed as light streaks along the length of the microneedles that approximately 10% of the coating remained on the microneedles. Surface examination of the treated skin showed an array of blue dots corresponding to microneedle penetration and coating deposition from the array.

For in vivo analysis, out-of-plane arrays of non-coated microneedles, made in Example 1, were autoclaved and manually applied onto the forearms of human subjects (n=3) for 30 s. Gentian violet was then applied to the treated site for 1 min and wiped away using isopropanol swabs. The gentian violet selectively stained the sites of skin perforation, which identified the sites of microneedle insertion. Dot arrays corresponding to array of microneedle penetrations were observed on the forearms. The subjects (n=3) did not report any discomfort upon insertion of the arrays.

One may reasonably infer from the results that arrays of microneedles can be coated with a solid drug formulation and integrated into a patch, which subsequently may be applied to human skin for delivery of drug into the skin without patient discomfort.

EXAMPLE 6

Fabrication of Microneedles with Various Coating Compositions

Stainless steel single microneedles, in-plane microneedle rows, or out-of-plane microneedle arrays were fabricated as described in Example 1. Various microneedle geometries were drafted in AutoCAD software (Autodesk, Cupertino, Calif., USA) and then cut into microneedles: single microneedles without pockets, single microneedles with three circular pockets each 90 µm in diameter, or single microneedles with a single rectangular pocket 400 µm long×50 µm wide; in-plane microneedle rows containing five microneedle shafts; or out-of-plane microneedle arrays with fifty microneedles. All needles were 730 µm in length and 180 µm in width. In-plane microneedle rows were fabricated, each with five rectangular (400 µm long×50 µm wide) pockets in the microneedle shafts.

Microneedle Coating

Using the custom designed dip-coating devices as in Example 1, the microneedles described in the preceding paragraph were uniformly coated, with spatial control over the length being coated. Single dips were made unless otherwise specified. The coated microneedles were allowed to air-dry at least 24 h before use.

The following aqueous formulations (weight/volume % unless specified otherwise) were prepared and used to coat the microneedles:

| | |
|---|---|
| Formulation A1 | 0.1% sulforhodamine |
| Formulation A2 | 1% carboxymethylcellulose sodium salt (CMC, low viscosity, USP grade, CarboMer, San Diego, CA, USA), 0.5% Lutrol F-68 NF (BASF, Mt. Olive, NJ, USA), 0.1% sulforhodamine (Molecular Probes, Eugene, OR, USA) |
| Formulation A3 | 52% (wt/wt %) sucrose, 0.2%(wt/wt %) Tween 20, 0.1% sulforhodamine |
| Formulation A4 | 0.1% sulforhodamine, 0.5% Lutrol F-68 NF, 0.5% hyaluronic acid |
| Formulation A5 | 0.1% sulforhodamine, 0.5% Lutrol F-68 NF, 0.5% xanthan gum |
| Formulation A6 | 0.1% sulforhodamine, 0.5% Lutrol F-68 NF, 1% sodium alginate |
| Formulation A7 | 0.1% sulforhodamine, 0.5% Lutrol F-68 NF, 5% polyvinylpyrrolidone |
| Formulation A8 | 0.1% sulforhodamine, 0.5% Lutrol F-68 NF, 52% (wt/wt %) sucrose |
| Formulation A9 | 25% sucrose, 0.1% sulforhodamine |
| Formulation A10 | 80% (vol/vol %) glycerol, 20% (vol/vol %) of 0.1% sulforhodamine |
| Formulation A11 | 1% carboxymethylcellulose sodium salt, 0.5%, Lutrol F-68 NF, 0.2%, sodium fluorescein |
| Formulation A12 | 80% (vol/vol %) glycerol, 20% (vol/vol %) green food dye |
| Formulation A13 | 80% (vol/vol %) glycerol, 20% (vol/vol %) amber food dye |
| Formulation A14 | 80% (vol/vol %) glycerol, 20% (vol/vol %) red food dye |

In addition, the following organic solvent formulations (weight/volume % unless specified otherwise) were prepared and used to coat the microneedles:

| | |
|---|---|
| Formulation O1 | 5% poly(lactic-co-glycolic acid) (PLGA) in acetonitrile |
| Formulation O2 | 5% polyvinylpyrrolidone, 0.1% curcumin in ethanol |
| Formulation O3 | 5% PLGA, 0.03% sulforhodamine in acetonitrile |

Effect of Viscosity and Surface Tension

To identify the effect of surface tension and viscosity on coating uniformity, two surfactant and viscosity enhancer systems were used to coat single microneedles (n=3) individually and then both combined using sulforhodamine as the model drug to help visualize the coatings. Dipped microneedles were air-dried for 24 hours and examined under Olympus IX70 fluorescent microscope with a CCD camera (RT Slider, Diagnostic Instruments, Sterling Heights, Mich., USA) to assess coating uniformity.

Attempts to coat with sulforhodamine in water (Formulation A1) did not produce a coating. Using sodium salt of carboxymethylcellulose or Lutrol F-68 NF, the coatings were found to be very thin (FIG. 6A) or localize away from the microneedle periphery towards the center (FIG. 6B), respectively. However, the combination (Formulation A2) produced good thick uniform coatings (FIG. 6C). A similar trend was observed for Formulation A3, as a thick uniform coating across the entire needle surface (FIG. 6F) was formed. A coating with only Tween 20 (a polyoxyethylene sorbitan monolaurate) solution containing sulforhodamine resulted in a very thin layer on the microneedle surface (FIG. 6D), while coating with only sucrose produced a coating which was more centralized on the microneedle shaft (FIG. 6E). The contraction of coating upon drying towards the center of the microneedle was more prominent in the case of sucrose as compared to carboxymethyl cellulose. Therefore, the presence of a surfactant was found to help spread the coating evenly across the microneedle surface, while the viscosity enhancer provided a thicker film of coating.

Drug-excipient interaction can lead to drug aggregation or decreased solubility. Scratching of Tween 20/sucrose based coatings on stainless steel microneedles with a hypodermic needle revealed a waxy characteristic which was not observed for Lutrol F-68/carboxymethylcellulose based coatings, apparently because Lutrol F-68 is a solid at room temperature while Tween 20 is a liquid. Therefore, the present formulations were based on Lutrol F-68 as the surfactant, and different viscosity enhancers were tested. Thick uniform coatings were formed using hyaluronic acid (Formulation A4), xanthan gum (Formulation A5), sodium alginate (Formulation A6), polyvinylpyrrolidone (Formulation A7) and sucrose (Formulation A8) as the viscosity enhancers. From this information, one may envision that concentrations of these or other viscosity enhancers or combinations thereof may be tailored using routine experimentation to produce coating solution characteristics specific for a wide variety different drug molecules.

EXAMPLE 7

Surface Modification of Microneedles by Precoating

In an effort to enhance the application of an aqueous coating solution to microneedles in a coating process without the use of a surfactant in the coating solution, the surface properties of the stainless steel microneedles produced in Example 6 were modified by (pre)coating the microneedles with a thin silicon dioxide layer (0.1 µm), in order to render the microneedle surface more hydrophilic. Silicon dioxide was deposited using a conventional vapor deposition method. Then, the microneedles were coated with an aqueous sulforhodamine solution. This resulted in a uniform but thin coating (less than 1 to 2 µm).

In another test, the stainless steel microneedles were (pre) coated with PLGA by dipping the microneedles in Formulation O1, in order to make the microneedles hydrophobic. After drying, these surface modified microneedles were dipped into Formulation A1, dried, and examined under a fluorescent microscope to check for coating uniformity. Unexpectedly, this surface modification also resulted in a uniform coating using just water and sulforhodamine solution. The coating was relatively thin (less than 1 to 2 µm), presumably because the coating solution did not include a viscosity enhancer, which it is would have yielded a thicker film and coating.

These results indicate that, for coating processes, the dynamic contact angle is more important than the static equilibrium contact angle. That is, during withdrawal of the microneedle from the coating solution, a liquid film becomes entrained on the PLGA surface. As the entrainment volume is small, the aqueous solvent rapidly evaporates to yield the solid coating. Surface modification of microneedles is a useful tool for controlling coating uniformity, and may be particularly well suited for sensitive protein solutions, given that protein solutions are often inherently viscous and will itself provide the necessary viscosity enhancement for thicker coatings.

EXAMPLE 8

Release of Hydrophobic Coating Materials from Microneedles

Single microneedles were coated with Formulation O2, as in Example 6, and examined under a fluorescent microscope for coating uniformity. A uniform coating of the microneedle surfaces resulted. The microneedles dipped in Formulation O2 were immersed in deionized (DI) water for 15 s and checked for loss of coating from the microneedle surface by visualization under the fluorescent microscope. After the water dipping, the coating was completely removed from the microneedles. Even though curcumin has negligible solubility in water, dissolution of the polyvinylpyrrolidone (the matrix of the solid coating) resulted in the microneedle coating coming off of the microneedle surface. PLGA coating (Formulation O3) also resulted in a uniform coating.

EXAMPLE 9

Coating Microneedles Using Molten Materials

Pocketed and unpocketed microneedles, made in Example 6, were dip coated into molten lidocaine and polyethylene glycol (PEG). Single microneedles with or without rectangular pockets (400 µm long×50 µm wide) were dipped in liquid molten solutions, which did not contain any solvent or additives, of lidocaine at 100° C. or PEG (MW 1500) at 55° C. each containing less than 0.01% sulforhodamine (added solely to help in coating visualization), cooled and air dried for 24 h, and examined under a fluorescent microscope for coating uniformity. The lidocaine molten solution was relatively viscous, and the resulting coatings covered the entire surface in both unpocketed and pocketed microneedles. PEG, however, produced coating only in the microneedle pocket. This phenomenon occurred because molten PEG has high surface tension. Using the molten liquid approach, microneedles can be coated with a variety of drugs in their pure state (e.g., lidocaine) or with drug-containing matrix materials without solvent by using a molten liquid as a dissolution medium for a solid drug (e.g., dexamathasone drug dissolved in molten PEG).

EXAMPLE 10

Coating Microneedles Having Pockets

Single microneedles having rectangular pockets (400 µm long and 50 µm wide) made as described in Example 6 were dipped into Formulation A2, Formulation A9, or Formulation A10. The process for coating the microneedles with Formulation A2 consisted of six dips with a temporal space of 6 s between dips. Coated microneedles were examined under a fluorescent microscope after drying for 24 hours.

With Formulation A2, both the pockets and the solid surface of microneedles were coated. However, with Formulation A9, which omits the surfactant from and increases the solids content in the coating solution, only the pockets of the microneedle were coated. Similarly, dipping microneedles in the viscous glycerol solution (Formulation A10) helped to fill the pockets without coating the microneedle surfaces. The liquid in the pockets completely evaporated in approximately 24 hours at ambient conditions.

In a similar process, microneedles were coated with propylene glycol, producing microneedles having liquid-filled pockets. These liquid pockets could be made more stable by storing under pressure in a nitrogen atmosphere. In one application of liquid-filled pocket microneedles, the liquid based drug formulations could deliver hydrophobic drugs from an organic solvent, such as polypropylene glycol.

EXAMPLE 11

Composite Coatings on Microneedles

Single microneedles with or without pockets were dipped in different formulations, as described in Example 6, in sequences to produce coatings of multiple molecules to generate different drug release profiles. Four different composite coating schemes were evaluated:

(1) pocketed microneedles with three circular pockets (90 µm diameter each) dipped into Formulation A12, DI water, Formulation A13, DI water, and Formulation A14 in that sequence. At each DI water step in Step (1), the portion of the microneedle dipped was decreased by one pocket to retain the formulation in it from the previous dip, while cleaning the water-dipped pockets. This procedure allowed sequential filling of each pocket with a different formulation. Between each dip and after completion of composite coatings, microneedles were allowed to dry and imaged under a fluorescent microscope;

(2) unpocketed microneedles dipped six times into Formulation O3 and then dipped six times into Formulation A11, which was intended to produce a device that can provide a release profile of a burst release followed by slow release;

(3) unpocketed microneedles dipped into Formulation A2, Formulation O1, and Formulation A11 in that sequence; and (4) microneedles with a rectangular pocket (400 µm×50 µm) dipped into Formulation A9, Formulation O1, and Formulation A11 in sequence.

After fabrication of the composite coated microneedles was completed, the microneedles were dipped into DI water for 1 min to assess dissolution/drug release. The dipping process caused the water-soluble layers to dissolve, leaving the PLGA layers intact on the microneedles. These composite coatings can therefore be tailored to meet drug delivery requirements either for bolus delivery or controlled delivery of single or multiple drugs.

EXAMPLE 12

Mass of Coating on Microneedles

To identify parameters important to controlling the total mass of coating (in order to control dosage), four coating parameters were varied in preparing coating microneedles, which were made as in Example 6. The parameters were (a) concentration of drug in the coating solution, (b) number of dips during coating, (c) number of microneedles in the array, and (d) pocketed or unpocketed microneedles for drug coated onto microneedles, with vitamin B as the model drug.

In-plane rows of microneedles were dipped into a solution containing 1% sodium salt of carboxymethyl cellulose, 0.5% Lutrol F-68 NF, and different concentrations of vitamin B. For parameter (a), vitamin B was used at 0.01%, 0.1%, 1%, 2%, 3%, and 4% concentrations (n=5 rows for each concentration) with 6 dips at 8 s interval. For parameter (b), a 3% vitamin B concentration was used with 1, 3, 6, 12, or 24 dips at 8 s intervals (n=5 rows for each dip number). For parameter (c), a 3% vitamin B concentration was used with out-of-plane arrays having 5 or 50 needles (n=3 arrays for each row number). For parameter (d), in-plane rows each with five microneedles having a rectangular pocket (400 μm×50 μm) were dipped into a formulation containing 1% or 3% vitamin B and 25% sucrose. All coated microneedles were allowed to dry for at least 24 hr and imaged using brightfield microscopy.

The mass of vitamin B in the coatings was then determined by dissolving the vitamin B containing coatings off of the microneedles and then measuring vitamin B concentration using fluorescence spectroscopy. The mass of vitamin B in the coatings was then calculated from the knowledge of the volume of DI water used to dissolve the coatings.

Figure 7A:
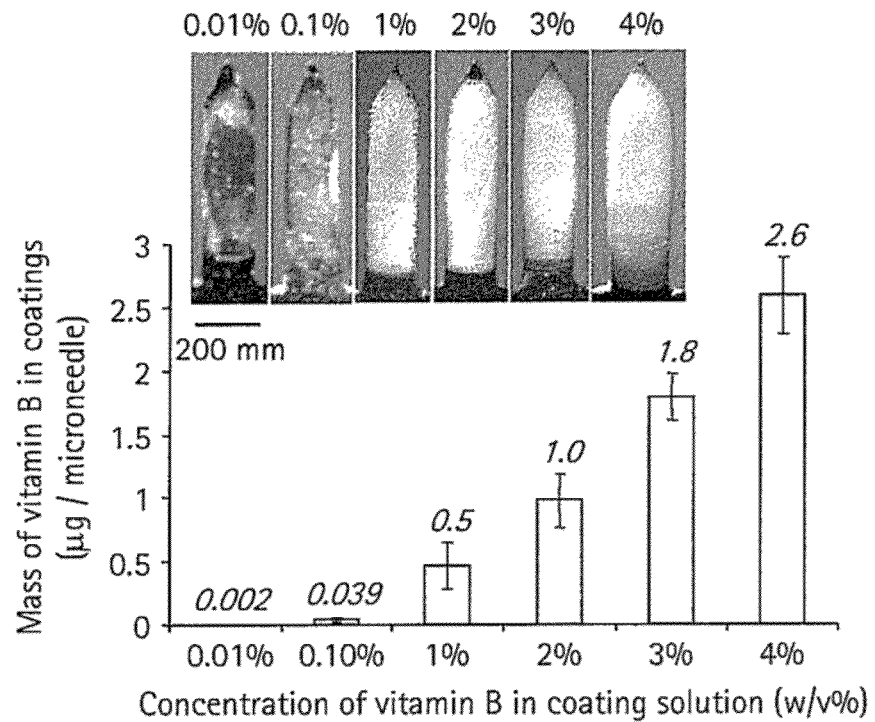
FIGS. 7A-7B are graphs indicating the mass of vitamin B coated on different microneedles in various embodiments.
Figure 7B:
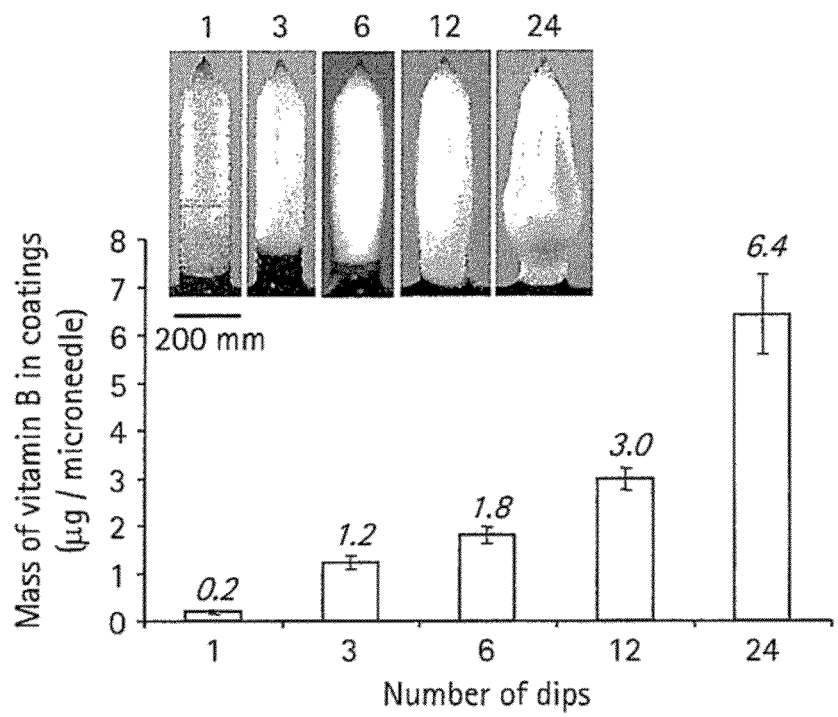

An increase in the concentration of vitamin B in the coating solution and in the number of coating dips was found to increase the mass of vitamin B coated onto microneedles and the thickness of coating, as illustrated in FIGS. 7A and 7B, respectively, with image insets showing thickness. At the maximum concentration of vitamin B used (i.e., 4%) with six dips, 2.6 μg of vitamin B was coated per microneedle. At the maximum number of dips used (i.e., 24) using a 3% solution concentration, the mass was 6.4 μg vitamin B per microneedle. Changing the number of microneedles from five to fifty increased the mass on the array proportionately, which suggests a consistent and uniform coating across the needles of the array. The use of pockets alone for microneedle coatings, led to vitamin B loading of 0.066 μg per microneedle.

Using either a single parameter or their combination, a pre-determined mass of vitamin B can be coated on the microneedles.

EXAMPLE 13

In Vitro Delivery of Coating Materials from Microneedles into Pig Skin

Single non-pocketed microneedles (n=3) coated with Formulation A2, and single pocketed (rectangular pocket—400 μm×50 μm) microneedles (n=3) coated with Formulation A10, as described in Example 6, were inserted into pig cadaver skin for 20 s and removed. After removing the microneedles, the skin surface was examined for coating residue using brightfield microscopy. In addition, the pig skin was examined histologically to assess the extent of delivery of microneedle coatings into the skin. Histological sections of pig skin after insertion of microneedles coated with Formulation A2 or Formulation A10 contain a tear in the skin corresponding to the penetration of the coated microneedles. The punctured spots are surrounded by a bright region around their periphery which indicates that the sulforhodamine was released from the solid coating or liquid in the pockets.

EXAMPLE 14

In vivo Insertion of Microneedle Arrays into Human Skin

Arrays of non-coated, out-of-plane microneedles were assembled into adhesive patches as described in Example 2, sterilized using ethylene oxide, and manually applied onto the forearms of human subjects (n=3). After removing the adhesive patch, Gentian violet was applied on the treated site for 1 min. and wiped away using isopropanol swabs. Gentian violet selectively stained the sites of skin perforation. Brightfield imaging of the skin surface after staining showed dark dots which correspond to insertion points of individual microneedles of the fifty needle array. The results of this example and the preceding one suggest that coated microneedle arrays will penetrate human skin and deliver their payload coatings.

Publications cited herein and the materials for which they are cited are specifically incorporated by reference. Modifications and variations of the methods and devices described herein will be obvious to those skilled in the art from the foregoing detailed description. Such modifications and variations are intended to come within the scope of the appended claims.

We claim:

1. A method for coating at least one microneedle comprising:
    providing a coating liquid disposed in one or more reservoirs, the coating liquid comprising at least one drug;
    providing a physical mask having one or more apertures extending therethrough, each aperture having cross-section dimensions larger than the at least one microneedle to be coated;
    aligning the at least one microneedle with at least one of the one or more apertures;
    inserting the at least one microneedle through the aligned aperture and into the coating liquid, thereby coating at least a portion of the microneedle; and
    removing the coated microneedle from the coating liquid and from the aperture.

2. The method of claim 1, wherein the physical mask comprises a plurality of holes or slits which closely circumscribe each microneedle or a single row of microneedles.

3. The method of claim 2, wherein the physical mask is in the form of a rigid plate secured to the reservoir.

4. The method of claim 1, wherein the one or more reservoirs are defined in a secondary structure.

5. The method of claim 1, wherein the step of inserting the microneedle through the aligned aperture is done before moving both the physical mask and the microneedle in a manner to cause the microneedle to be dipped into the coating liquid.

6. The method of claim 1, further comprising inserting the at least one microneedle into the same or a different coating liquid and then removing the microneedle from said same or different coating liquid.

7. The method of any claim 1, wherein the at least one microneedle comprises one or more pockets therein.

8. The method of claim 7, wherein the process coats substantially only the one or more pockets.

9. The method of claim 1, wherein the coating liquid in the reservoir is agitated or flowed to maintain composition uniformity.

10. The method of claim 1, wherein the surface energy of the coating liquid is less than the surface energy of the at least one microneedle.

11. The method of claim 1, wherein the coating liquid further comprises a viscosity enhancer.

12. The method of claim 11, wherein the coating liquid further comprises a surfactant.

13. The method of claim 1, wherein the coating liquid is heterogeneous.

14. The method of claim 1, wherein the at least one microneedle is formed of stainless steel, titanium, or another metal.

15. The method of claim 1, wherein the at least one microneedle is formed of a biodegradable polymer.

16. The method of claim 1, wherein the at least one microneedle comprises two or more microneedles.

17. The method of claim 1, wherein the drug comprises a therapeutic or prophylactic agent.

18. The method of claim 1, further comprising solidifying the liquid coating remaining on the microneedle after removing the coated microneedle from the coating liquid and from the aperture.

19. The method of claim 18, wherein the at least one microneedle comprises an array of 2 to 1000 microneedles having beveled or tapered tips.

20. The method of claim 19, wherein the microneedles comprising a biodegradable polymer.

21. The method of claim 19, wherein the coating liquid comprises a sugar.

22. The method of claim 19, wherein the drug comprises a vaccine.

23. The method of claim 19, wherein the coating liquid comprises a sugar and the drug comprises a vaccine.

24. The method of claim 19, wherein the solidified coating is adapted to come off the microneedle following insertion into a biological tissue.

* * * * *